US011696892B2

(12) United States Patent
Hansson et al.

(10) Patent No.: US 11,696,892 B2
(45) Date of Patent: Jul. 11, 2023

(54) LIPID NANOPARTICLES FOR DELIVERING MODIFIED RNA ENCODING A VEGF-A POLYPEPTIDE

(71) Applicant: ModernaTX, Inc., Cambridge, MA (US)

(72) Inventors: Kenny Mikael Hansson, Mölndal (SE); Kerry Benenato, Sudbury, MA (US); Maria Wågberg, Mölndal (SE); Annika Pålsson, Mölndal (SE); Regina Fritsche-Danielson, Mölndal (SE)

(73) Assignee: ModernaTX, Inc., Cambridge, MA (US)

(*) Notice: Subject to any disclaimer, the term of this patent is extended or adjusted under 35 U.S.C. 154(b) by 28 days.

(21) Appl. No.: 16/760,406

(22) PCT Filed: Oct. 31, 2018

(86) PCT No.: PCT/US2018/058541
§ 371 (c)(1),
(2) Date: Apr. 29, 2020

(87) PCT Pub. No.: WO2019/089818
PCT Pub. Date: May 9, 2019

(65) Prior Publication Data
US 2020/0338004 A1  Oct. 29, 2020

Related U.S. Application Data

(60) Provisional application No. 62/579,671, filed on Oct. 31, 2017.

(51) Int. Cl.
*A61K 9/127* (2006.01)
*A61P 43/00* (2006.01)
(Continued)

(52) U.S. Cl.
CPC .......... *A61K 9/1272* (2013.01); *A61K 9/0019* (2013.01); *A61K 31/7088* (2013.01);
(Continued)

(58) Field of Classification Search
None
See application file for complete search history.

(56) References Cited

U.S. PATENT DOCUMENTS 9,034,316 B2   5/2015 Pecora et al.
9,867,888 B2 * 1/2018 Benenato ............. C07D 277/38
(Continued)

FOREIGN PATENT DOCUMENTS

CN     102341498      2/2012
CN     105451779      3/2016
(Continued)

OTHER PUBLICATIONS

Derek Lowe. "What mRNA is Good for, and What It Maybe Isn't." https://www.science.org/content/blog-post/what-mrna-good-and-what-it-maybe-isn-t accessed Sep. 1, 2021, originally published Jun. 29, 2021, pp. 1-14. (Year: 2021).*
(Continued)

*Primary Examiner* — Isaac Shomer
(74) *Attorney, Agent, or Firm* — Fish & Richardson P.C.

(57) ABSTRACT

The disclosure relates to nanoparticles comprising a lipid component and a modified RNA encoding a VEGF-A polypeptide. Aspects of the disclosure further relate to uses of nanoparticles comprising a lipid component and a modified RNA encoding a VEGF-A polypeptide, for improving wound healing in a subject.

16 Claims, 8 Drawing Sheets

Figure 1:
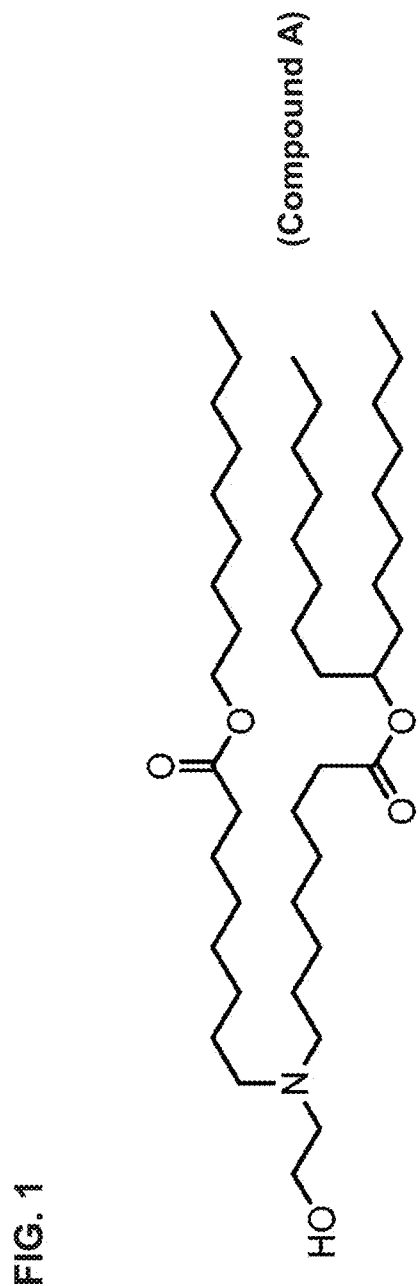

Specification includes a Sequence Listing.

5'-Cap  5'-UTR  Start  Coding Region  Stop  3'-UTR  Poly (A) tail

5' $^{7Me}G_{ppp}G_{2'OMe}$ GGAAAUAAGAGAGAAAAGAAGAGUAAGAAGAAAUAUAAGAGCCACCAUGAACUUUCUGCUGUCUUG
GGUGCAUUGGAGCCUUGCCUUGCUGCUCUACCUCCACCAUGCCAAGUGGUCCCAGGCUGCACCCAUGGCAGAAG
GAGGAGGGCAGAAUCAUCACGAAGUGGUGAAGUUCAUGGAUGUCUAUCAGCGCAGCUACUGCCAUCCAAUCGAG
ACCCUGGUGGACAUCUUCCAGGAGUACCCUGAUGAGAUCGAGUACAUCUUCAAGCCAUCCUGUGUGUGCCCUGAU
GCGAUGCGGGGCUGCUGCAAUGACGAGGGCCUGGAGUGUGUGCCCACUGAGGAGUCCAACAUCACCAUGCAG
AUUAUGCGGAUCAAACCUCACCAAGGCCAGCACAUAGGAGAGAUGAGCUUCCUACAGCACAACAAAUGUGAAUGC
AGACCAAAGAAAGAUAGAGCAAGACAAGAAAAUCCCUGUGGGCCUUGCUCAGAGCGGAGAAAGCAUUUGUUUGUA
CAAGAUCCGCAGACGUGUAAAUGUUCCUGCAAAAACACAGACUCGCGUUGCAAGGCGAGGCAGCUUGAGUUAAAC
GAACGUACUUGCAGUGUGACAAGCCGAGGCGGUGAUAAUAGGCGUGGCCAUGCUUCUUGCCCC
UUGGGCCUCCCCCAGCCCUCUCCCCUUCCUGCACCCGUACCCCCGUGGUCUUUGAAUAAAGUCUGAGUGGG
CGGCAAAAAAAAAAAAAAAAAAAAAAAAAAAAAAAAAAAAAAAAAAAAAAAAAAAAAAAAAAAAAAAAAAAAAAA
AAAAAAAAAAAAAAAAAAAAAAAAUCUAG$_{OH}$3' (SEQ ID NO: 1)

Wherein:
A, C, G & U= AMP, CMP, GMP & N1-methyl-pseudoUMP, respectively
Me = methyl
p = inorganic phosphate

(51) Int. Cl.
  *A61K 31/7088* (2006.01)
  *A61K 38/18* (2006.01)
  *B82Y 5/00* (2011.01)
  *A61K 9/00* (2006.01)
(52) U.S. Cl.
  CPC .......... *A61K 38/1866* (2013.01); *A61P 43/00* (2018.01); *B82Y 5/00* (2013.01)

(56) References Cited

U.S. PATENT DOCUMENTS

| | | | |
|---|---|---|---|
| 9,868,691 B2* | 1/2018 | Benenato | C07K 14/505 |
| 9,868,692 B2* | 1/2018 | Benenato | C07D 271/06 |
| 9,868,693 B2* | 1/2018 | Benenato | A61P 9/00 |
| 10,266,485 B2* | 4/2019 | Benenato | A61P 31/00 |
| 10,442,756 B2* | 10/2019 | Benenato | A61P 25/00 |
| 2008/0171711 A1 | 7/2008 | Hoerr et al. | |
| 2013/0156849 A1* | 6/2013 | de Fougerolles | A61P 35/00 424/94.64 |
| 2013/0259923 A1* | 10/2013 | Bancel | C07K 14/745 530/358 |
| 2014/0073687 A1* | 3/2014 | Chien | A61P 37/06 514/44 R |
| 2014/0275229 A1* | 9/2014 | Bancel | C12N 9/1051 435/193 |
| 2015/0246139 A1* | 9/2015 | Bancel | A61K 9/1277 435/69.6 |
| 2016/0046685 A1* | 2/2016 | Nolta | C07K 14/475 435/235.1 |
| 2018/0002393 A1* | 1/2018 | Bancel | A61K 48/0033 |
| 2020/0407411 A1 | 12/2020 | Parinder et al. | |
| 2022/0226438 A1 | 7/2022 | Hansson et al. | |

FOREIGN PATENT DOCUMENTS

| | | | |
|---|---|---|---|
| JP | 2014-511694 | 5/2014 | |
| RU | 2550959 | 5/2015 | |
| WO | WO 2010/065671 | 6/2010 | |
| WO | WO 2011/069529 | 6/2011 | |
| WO | WO 2012/103985 | 8/2012 | |
| WO | WO 2012/138453 | 10/2012 | |
| WO | WO 2014/152211 | 9/2014 | |
| WO | WO 2015/024667 | 2/2015 | |
| WO | WO 2015/107026 | 7/2015 | |
| WO | WO 2016/118725 A1 | 7/2016 | |
| WO | WO 2017/049245 | 3/2017 | |
| WO | WO-2017049245 A2 * | 3/2017 | ........... C07C 233/72 |
| WO | WO 2017/214175 A1 | 12/2017 | |
| WO | WO-2017214175 A1 * | 12/2017 | ......... A61K 31/7115 |
| WO | WO 2018/104540 | 6/2018 | |
| WO | WO 2018/104874 | 6/2018 | |
| WO | WO 2019/0089818 A1 | 5/2019 | |

OTHER PUBLICATIONS

Businesswire https://www.businesswire.com/news/home/20160726005317/en/AstraZeneca-Moderna-Announce-Filing-Clinical-Trial-Application accessed Nov. 8, 2021, originally published Jul. 26, 2016, 2 printed pages. (Year: 2016).*
Asher Mullard. "mRNA-based drug approaches Phase I milestone." Nature Reviews Drug Discovery, vol. 15, Sep. 2016, p. 595, published online Aug. 30, 2016. (Year: 2016).*
Vesa Anttila et al. "Synthetic mRNA Encoding VEGF-A in Patients Undergoing Coronary Artery Bypass Grafting: Design of a Phase 2a Clinical Trial." Molecular Therapy Methods & Clinical Development, vol. 18, Sep. 2020, pp. 464-472. (Year: 2020).*
United States Court of Appeals for the Federal Circuit. "In re *James F. Crish and Richard L. Eckert.*" Case 04/1075, U.S. Appl. No. 08/822,509, decided Dec. 21, 2004, pp. 1-12 and a cover page. (Year: 2004).*
US Patent and Trademark Office, *Bayer Cropscience LP* v. *Syngenta Limited*. Case IPR2017-01332, Apr. 2, 2018, pp. 1-7. (Year: 2018).*
Kenneth R. Chien, et al. "Synthetic Chemically Modified mRNA (modRNA): Toward a New Technology Platform for Cardiovascular Biology and Medicine", Cold Spring Har Perspect Med, 2014, 10 pages (1-10).
Kenny Hansson, "VEGF-A modified mRNA in diabetic wound healing and future treatment opportunities", Presentation at 4th International mRNA Health Conference, Boston, Nov. 1, 2016, 11 pages.
Lior Zangi, et al., "Modified mRNA directs the fate of heart progenitor cells and induces vascular regeneration after myocardial infarction", Nature Biotechnology, vol. 31, No. 10, pp. 898-911, Oct. 2013.
PCT International Search Report dated Feb. 12, 2019, issued in corresponding International Application No. PCT/US2018/058541, 4 pages.
PCT International Search Report issued in International Application No. PCT/US2020/032241 dated Sep. 9, 2020, 7 pgs.
PCT Written Opinion of the International Searching Authority issued in PCT/US2020/032241 dated Sep. 9, 2020, 9 pgs.
Carlsson et al., "Biocompatible, Purified VEGF-A mRNA Improves Cardiac Function after Intracardiac Injection One Week Post-Myocardial Infarction in Swine," Molecular Therapy Methods & Clinical Development, Apr. 2018, 9:330-346.
Chinese Office Action issued by the Chinese Patent Office in Application No. CN 201780048447.8, dated Nov. 1, 2021, 26 pages.
Coelho et al., "Safety and Efficacy of RNAi Therapy for Transthyretin Amyloidosis," N. Eng. J. Med., Aug. 2013, 369(9):819-829.
Extended European Search Report issued in European Application No. 21186195.0 dated Feb. 17, 2022, 16 pages.
International Preliminary Report on Patentability in International Application No. PCT/US2017/036188, dated Dec. 11, 2018, 13 pages.
International Preliminary Report on Patentability in International Application No. PCT/US2018/058541, dated May 20, 2020, 6 pages.
International Search Report in International Application No. PCT/US2017/036188, dated Nov. 23, 2017, 9 pages.
Kaczmarek et al., "Advances in the delivery of RNA therapeutics: from concept to clinical reality," Genome Med., Jun. 2017, 9:60:1-16.
Lisa et al., "Double-stranded ribonucleic acid from carnation cryptic virus," Virology, Dec. 1, 1981, 115(2):410-13.
Lui et al., "Driving vascular endothelial cell fate of human multipotent Isl1+ heart progenitors with VEGF modified mRNA," Cell Research, Oct. 2013, 23(10):1172-1186.
NCBI Reference No. XM_004044088.3, "Predicted—Gorilla gorilla gorilla vascular endothelial growth factor A, transcript variant 1 (VEGFA), mRNA," Sep. 30, 2019, 2 pages.
Probst et al., "Spontaneous cellular uptake of exogenous messenger RNA in vivo is nucleic acid-specific, saturable and ion dependent," Gene Therapy, May 3, 2007, 14(15):1175-80.
Rudin et al., "Delivery of a Liposomal c-raf-1 Antisense Oligonucleotide by Weekly Bolus Dosing in Patients with Advanced Solid Tumors: A Phase I Study," Clin. Cancer Res., Nov. 2004, 10(21):7244-7251.
Sun et al., "Modified VEGF-A mRNA induces sustained multifaceted microvascular response and accelerates diabetic wound healing," Sci Rep., 2018, 8(17509): 1-11.
Xue et al., "Lipid-Based Nanocarriers for RNA Delivery," Curr. Pharm Des., Nov. 2015, 21(22):3140-3147.
Zhang et al., "Implications of pharmacokinetic behavior of lipoplex for its inflammatory toxicity," Adv. Drug Deliv. Rev., Apr. 2005, 57(5):689-698.
Zytkovicz et al., "Factors influencing the covalent binding of (±) 7-b, 8-a-dihydroxy-9-a, 1O-a-epoxy-7,8,9,10-tetrahydrobenzo[a]pyrene to RNA," Molecular Pharmacology, Sep. 1984, 26(2):369-75.
Adachi et al., "Determinants of Left Ventricular Systolic Function Improvement Following Coronary Artery Revascularization in Heart Failure Patients With Reduced Ejection Fraction (HFrEF)," Int. Heart J., Sep. 2016, 57(5):565-72.
International Preliminary Report on Patentability in International Application No. PCT/US2020/032241, dated Nov. 2, 2021, 10 pages.

(56) References Cited

OTHER PUBLICATIONS

International Preliminary Report on Patentability issued in International Application No. PCT/US2020/032126, dated Nov. 22, 2021, 12 pages.

International Search Report in International Application No. PCT/US2020/032126, dated Sep. 14, 2020, 8 pages.

Järveläinen et al., "Citrate-Saline-Formulated mRNA Delivery into the Heart Muscle with an Electromechanical Mapping and Injection Catheter Does Not Lead to Therapeutic Effects in a Porcine Chronic Myocardial Ischemia Model," Human Gene Therapy, Oct. 2021, 32(19-20), 1295-1307.

Minutti et al., "A Macrophage-Pericyte Axis Directs Tissue Restoration via Amphiregulin-Induced Transforming Growth Factor Beta Activation," Immunity, Mar. 2019, 50(3):645-654.

Mitrut et al., "Histopathological Aspects of the Myocardium in Dilated Cardiomyopathy,"Curr Health Sci J., 2018, 44(3):243-249.

Seferović et al., "Heart failure in cardiomyopathies: a position paper from the Heart Failure Association of the European Society of Cardiology," European Journal of Heart Failure, May 2019, 21(5):553-576.

Third Party Observation issued in International Application No. PCT/US2020/032126, dated May 22, 2021, 2 pages.

Weintraub et al., "Dilated cardiomyopathy," The Lancet, Jul. 2017, 390(10092):400-414.

Written Opinion of the International Searching Authority issued in International Application No. PCT/US2017/036188, dated Nov. 23, 2017, 12 pages.

Written Opinion of the International Searching Authority issued in International Application No. PCT/US2020/032126, dated Sep. 14, 2020, 11 pages.

\* cited by examiner

FIG. 2A

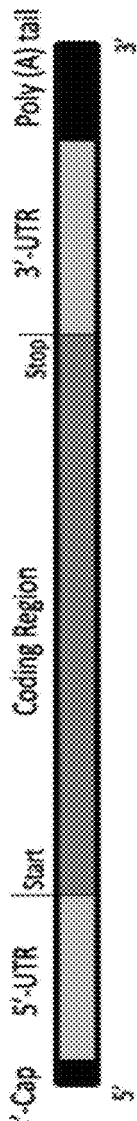

FIG. 2B

5'^{7Me}G_{ppp}G_{2'OMe}GGAAAUAAGAGAGAAAAGAAGAGUAAAUAUAAGAGCCACCAUGAACUUUCUGCUGUCUUG
GGUGCAUUGGAGCCUUGCUGCUCUACCUCCACCAUGCCAAGGUCCAGGCUGCACCCAUGGCAGAAG
GAGGAGGGCAGAAUCAUCAGAGGUGAAGUUCAUGGAUGAGUUCUACGCAGUCUACGCAUCCAAUCGAG
ACCCUGGUGGACAUCCAGGAGUACCUGCAAUCAGCACAUCUUCAGCCAUCUGUGCCCUGAU
GCGAUGCGGGGGCUGCAAUCACCAAGGACAAGCAAGGCCAGCAAGAGGAGCCUACAGAGCGAAGCAUUGUUGUA
AUUAUGCGGAUCAAAGAUAAGAGACAAGAAACGUCCUGCAAAAUGUUCCUGAGGCGGUAAAUAUGGCGGUUGAGGCAGCCUUGUGAGUAAAC
GAACGUACUUGCAGAGUGACAAGCCGGUGAUAAUAGGCUGGAGCCCUGCGUUGGCCAUGCGUCUUGCCCC
UUGGGCCCUCCCCAGCCCCGGUACCCCGGUACCCCCUUCCUGCACCCCGGUGAAUAAAGUCUGAGUGGG
CGGCAAAAAAAAAAAAAAAAAAAAAAAAAAAAAUCUAG_{OH}3' (SEQ ID NO: 1)

Wherein:
A, C, G & U= AMP, CMP, GMP & N1-methyl-pseudoUMP, respectively
Me = methyl
p = inorganic phosphate

LIPID NANOPARTICLES FOR DELIVERING MODIFIED RNA ENCODING A VEGF-A POLYPEPTIDE

1. CROSS-REFERENCE TO RELATED APPLICATIONS

This application is the U.S. national phase entry under 35 U.S.C. § 371 of PCT International Application No. PCT/US2018/058541, filed on Oct. 31, 2018, which claims priority to U.S. Provisional Application No. 62/579,671, filed on Oct. 31, 2017, the entire contents of which are herein incorporated by reference

2. SEQUENCE LISTING

The instant application contains a Sequence Listing which has been submitted electronically in ASCII format and is hereby incorporated by reference in its entirety. Said ASCII copy, created on Oct. 31, 2018, is named 09963_0092_00304_SL.txt and is 11,396 bytes in size.

3. FIELD

The disclosure relates to nanoparticles comprising a lipid component and a modified RNA encoding a VEGF-A polypeptide. Aspects of the disclosure further relate to uses of nanoparticles comprising a lipid component and a modified RNA encoding a VEGF-A polypeptide for improving wound healing in a subject.

4. BACKGROUND

Vascular endothelial growth factor A (VEGF-A) pathways play a central role in the wound healing process, including revascularization of damaged tissues, improving vascular permeability, and formation of new blood vessels (angiogenesis). It remains challenging to deliver agents to augment VEGF-A pathways for potential therapeutic effects such as improving wound healing in a subject.

A diverse number of methods has been attempted to allow clinically tractable approaches to increase VEGF-A proteins in target tissues. However, each of the approaches has significant drawbacks. For instance, systemic VEGF-A protein delivery can result in significant hypotension and VEGF-A is rapidly degraded. Viral encapsulated and naked VEGF-A DNA plasmids have limited temporal control of protein expression and the efficiency of in vivo expression can be highly variable and non-dose dependent. As a result, these limitations have restricted the applicability of augmenting VEGF-A levels as a therapeutic agent.

Another recent development is to deliver therapeutic RNAs encoding VEGF-A proteins. However, delivery of natural RNAs to cells can be challenging due to the relative instability and low cell permeability of such RNA molecules. Also, natural RNAs can trigger immune activation (See, e.g., Kaczmarek et al., "Advances in the delivery of RNA therapeutics: from concept to clinical reality," Genome Med., 2017, 9: 60), which limit their uses for delivering VEGF-A proteins to target tissues.

Accordingly, there remains a need for compositions that allow for effective and safe delivery of RNAs encoding VEGF-A proteins. In addition, there remains a need for alternative methods to augment VEGF-A pathways for potential therapeutic effects such as improving wound healing in a subject.

5. SUMMARY

The disclosure relates to nanoparticles comprising a lipid component and a modified RNA encoding a VEGF-A polypeptide. Aspects of the disclosure further relate to uses of nanoparticles comprising a lipid component and a modified RNA encoding a VEGF-A polypeptide, for improving wound healing in a subject.

Certain embodiments of the present disclosure are summarized in the following paragraphs. This list is only exemplary and not exhaustive of all of the embodiments provided by this disclosure.

Embodiment 1. A nanoparticle comprising
(i) a lipid component comprising a compound having the structure

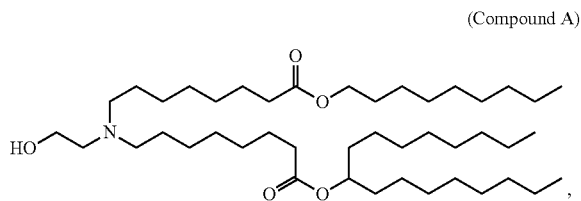 [SMILES: CCCCCCCCCOC(=O)CCCCCCCN(CCO)CCCCCCCC(=O)OC(CCCCCCCC)CCCCCCCC]

(Compound A)

and
(ii) a modified RNA comprising any one of SEQ ID NOs: 1 and 3-5, encoding a VEGF-A polypeptide of SEQ ID NO: 2.

Embodiment 2. The nanoparticle of embodiment 1, wherein the lipid component further comprises a phospholipid, a structural lipid, and/or a PEG lipid.

Embodiment 3. The nanoparticle of embodiment 2, wherein the phospholipid is selected from the group consisting of 1,2-distearoyl-sn-glycero-3-phosphocholine (DSPC), 1,2-dioleoyl-sn-glycero-3-phosphoethanolamine (DOPE), 1,2-dilinoleoyl-sn-glycero-3-phosphocholine (DLPC), 1,2-dimyristoyl-sn-glycero-phosphocholine (DMPC), 1,2-dioleoyl-sn-glycero-3-phosphocholine (DOPC), 1,2-dipalmitoyl-sn-glycero-3-phosphocholine (DPPC), 1,2-diundecanoyl-sn-glycero-phosphocholine (DUPC), 1-palmitoyl-2-oleoyl-sn-glycero-3-phosphocholine (POPC), 1,2-di-O-octadecenyl-sn-glycero-3-phosphocholine (18:0 Diether PC), 1-oleoyl-2-cholesterylhemisuccinoyl-sn-glycero-3-phosphocholine (OChemsPC), 1-hexadecyl-sn-glycero-3-phosphocholine (C16 Lyso PC), 1,2-dilinolenoyl-sn-glycero-3-phosphocholine, 1,2-diarachidonoyl-sn-glycero-3-phosphocholine, 1,2-didocosahexaenoyl-sn-glycero-3-phosphocholine, 1,2-diphytanoyl-sn-glycero-3-phosphoethanolamine (ME 16.0 PE), 1,2-distearoyl-sn-glycero-3-phosphoethanolamine, 1,2-dilinoleoyl-sn-glycero-3-phosphoethanolamine, 1,2-dilinolenoyl-sn-glycero-3-phosphoethanolamine, 1,2-diarachidonoyl-sn-glycero-3-phosphoethanolamine, 1,2-didocosahexaenoyl-sn-glycero-3-phosphoethanolamine, 1,2-dioleoyl-sn-glycero-3-phospho-rac-(1-glycerol) sodium salt (DOPG), sphingomyelin, and mixtures thereof;
the structural lipid is selected from the group consisting of cholesterol, fecosterol, sitosterol, ergosterol, campesterol, stigmasterol, brassicasterol, tomatidine, ursolic acid, alpha-tocopherol, and mixtures thereof; and/or
the PEG lipid is selected from the group consisting of a PEG-modified phosphatidylethanolamine, a PEG-modified phosphatidic acid, a PEG-modified ceramide, a PEG-modified dialkylamine, a PEG-modified diacylglycerol, a PEG-modified dialkylglycerol, and mixtures thereof.

Embodiment 4. The nanoparticle of embodiment 1, wherein the lipid component further comprises a phospholipid that is DSPC, a structural lipid that is cholesterol, and/or a PEG lipid that is PEG-DMG.

Embodiment 5. The nanoparticle according to any one of embodiments 1-4, wherein the N:P ratio is from about 2:1 to about 30:1.

Embodiment 6. The nanoparticle of embodiment 5, wherein the N:P ratio is about 5.67:1.

Embodiment 7. The nanoparticle of embodiment 5, wherein the N:P ratio is about 3:1.

Embodiment 8. The nanoparticle according to any one of embodiments 1-4, wherein the wt/wt ratio of the lipid component to the modified RNA is from about 10:1 to about 100:1.

Embodiment 9. The nanoparticle of embodiment 8, wherein the wt/wt ratio of the lipid component to the modified RNA is about 20:1.

Embodiment 10. The nanoparticle of embodiment 8, wherein the wt/wt ratio of the lipid component to the modified RNA is about 10:1.

Embodiment 11. The nanoparticle according to any one of embodiments 1-4, wherein the nanoparticle has a mean diameter from about 50 nm to 100 nm.

Embodiment 12. A pharmaceutical composition comprising
(a) at least one nanoparticle comprising (i) a lipid component comprising a compound having the structure

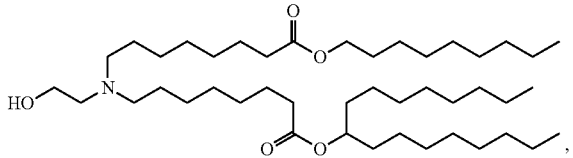

(Compound A)

and (ii) a modified RNA comprising any one of SEQ ID NOs: 1 and 3-5, encoding a VEGF-A polypeptide of SEQ ID NO: 2; and
(b) a pharmaceutically acceptable excipient.

Embodiment 13. The pharmaceutical composition of embodiment 12, wherein the lipid component further comprises a phospholipid, a structural lipid, and/or a PEG lipid.

Embodiment 14. The pharmaceutical composition of embodiment 13, wherein the phospholipid is selected from the group consisting of 1,2-distearoyl-sn-glycero-3-phosphocholine (DSPC), 1,2-dioleoyl-sn-glycero-3-phosphoethanolamine (DOPE), 1,2-dilinoleoyl-sn-glycero-3-phosphocholine (DLPC), 1,2-dimyristoyl-sn-glycero-phosphocholine (DMPC), 1,2-dioleoyl-sn-glycero-3-phosphocholine (DOPC), 1,2-dipalmitoyl-sn-glycero-3-phosphocholine (DPPC), 1,2-diundecanoyl-sn-glycero-phosphocholine (DUPC), 1-palmitoyl-2-oleoyl-sn-glycero-3-phosphocholine (POPC), 1,2-di-O-octadecenyl-sn-glycero-3-phosphocholine (18:0 Diether PC), 1-oleoyl-2-cholesterylhemisuccinoyl-sn-glycero-3-phosphocholine (OChemsPC), 1-hexadecyl-sn-glycero-3-phosphocholine (C16 Lyso PC), 1,2-dilinolenoyl-sn-glycero-3-phosphocholine, 1,2-diarachidonoyl-sn-glycero-3-phosphocholine, 1,2-didocosahexaenoyl-sn-glycero-3-phosphocholine, 1,2-diphytanoyl-sn-glycero-3-phosphoethanolamine (ME 16.0 PE), 1,2-distearoyl-sn-glycero-3-phosphoethanolamine, 1,2-dilinoleoyl-sn-glycero-3-phosphoethanolamine, 1,2-dilinolenoyl-sn-glycero-3-phosphoethanolamine, 1,2-diarachidonoyl-sn-glycero-3-phosphoethanolamine, 1,2-didocosahexaenoyl-sn-glycero-3-phosphoethanolamine, 1,2-dioleoyl-sn-glycero-3-phospho-rac-(1-glycerol) sodium salt (DOPG), sphingomyelin, and mixtures thereof;
the structural lipid is selected from the group consisting of cholesterol, fecosterol, sitosterol, ergosterol, campesterol, stigmasterol, brassicasterol, tomatidine, ursolic acid, alpha-tocopherol, and mixtures thereof; and/or
the PEG lipid is selected from the group consisting of a PEG-modified phosphatidylethanolamine, a PEG-modified phosphatidic acid, a PEG-modified ceramide, a PEG-modified dialkylamine, a PEG-modified diacylglycerol, a PEG-modified dialkylglycerol, and mixtures thereof.

Embodiment 15. The pharmaceutical composition of embodiment 12, wherein the lipid component further comprises a phospholipid that is DSPC, a structural lipid that is cholesterol, and/or a PEG lipid that is PEG-DMG.

Embodiment 16. The pharmaceutical composition according to any one of embodiments 12-15, wherein the N:P ratio is from about 2:1 to about 30:1.

Embodiment 17. The pharmaceutical composition of embodiment 16, wherein the N:P ratio is about 5.67:1.

Embodiment 18. The pharmaceutical composition of embodiment 16, wherein the N:P ratio is about 3:1.

Embodiment 19. The pharmaceutical composition according to any one of embodiments 12-18, wherein the wt/wt ratio of the lipid component to the modified RNA is from about 10:1 to about 100:1.

Embodiment 20. The pharmaceutical composition of embodiment 19, wherein the wt/wt ratio of the lipid component to the modified RNA is about 20:1.

Embodiment 21. The pharmaceutical composition of embodiment 19, wherein the wt/wt ratio of the lipid component to the modified RNA is about 10:1.

Embodiment 22. The pharmaceutical composition according to any one of embodiments 12-21, wherein the nanoparticle has a mean diameter from about 50 nm to 100 nm.

Embodiment 23. The pharmaceutical composition according to any one of embodiments 12-22, wherein when administered to a mammalian tissue or a subject, the pharmaceutical composition results in a maximum observed plasma and/or tissue concentration, $C_{max}$, of the VEGF-A polypeptide of SEQ ID NO: 2 up to about 450 pg/ml plasma or pg/mg tissue.

Embodiment 24. The pharmaceutical composition according to any one of embodiments 12-22, wherein when administered to a mammalian tissue or a subject, the pharmaceutical composition results in a plasma and/or tissue total area under the concentration curve, $AUC_{0-t}$, of the VEGF-A polypeptide of SEQ ID NO: 2 up to about 5,500 pg*h/ml plasma or pg*h/mg tissue.

Embodiment 25. The pharmaceutical composition according to any one of embodiments 12-22, wherein when administered to a mammalian tissue or a subject, the pharmaceutical composition results in the production of more than about 400 pg/mg tissue of the VEGF-A polypeptide of SEQ ID NO: 2 within 8 hours.

Embodiment 26. The pharmaceutical composition according to any one of embodiments 12-22, wherein when administered to a mammalian tissue or a subject, the pharmaceutical composition results in the production of more than about 1 pg/mg tissue of the VEGF-A polypeptide of SEQ ID NO: 2 for up to 6 days.

Embodiment 27. The pharmaceutical composition of embodiment 12, wherein the pharmaceutically acceptable excipient is chosen from a solvent, dispersion media, diluent, dispersion, suspension aid, surface active agent, isotonic agent, thickening or emulsifying agent, preservative, polymer, peptide, protein, cell, hyaluronidase, and mixtures thereof.

Embodiment 28. A method for promoting and/or improving wound healing in a subject, comprising administering to the subject an effective amount of the nanoparticle according to any one of embodiments 1-11 or the pharmaceutical composition according to any one of embodiments 12-27.

Embodiment 29. The method of embodiment 28, wherein the lipid component of the nanoparticle further comprises a phospholipid, a structural lipid, and a PEG lipid.

Embodiment 30. The method of embodiment 29, wherein the phospholipid is selected from the group consisting of 1,2-distearoyl-sn-glycero-3-phosphocholine (DSPC), 1,2-dioleoyl-sn-glycero-3-phosphoethanolamine (DOPE), 1,2-dilinoleoyl-sn-glycero-3-phosphocholine (DLPC), 1,2-dimyristoyl-sn-gly cero-phosphocholine (DMPC), 1,2-dioleoyl-sn-glycero-3-phosphocholine (DOPC), 1,2-dipalmitoyl-sn-glycero-3-phosphocholine (DPPC), 1,2-diundecanoyl-sn-glycero-phosphocholine (DUPC), 1-palmitoyl-2-oleoyl-sn-glycero-3-phosphocholine (POPC), 1,2-di-O-octadecenyl-sn-glycero-3-phosphocholine (18:0 Diether PC), 1-oleoyl-2 cholesterylhemisuccinoyl-sn-glycero-3-phosphocholine (OChemsPC), 1-hexadecyl-sn-glycero-3-phosphocholine (C16 Lyso PC), 1,2-dilinolenoyl-sn-glycero-3-phosphocholine, 1,2-diarachidonoyl-sn-glycero-3-phosphocholine, 1,2-didocosahexaenoyl-sn-glycero-3-phosphocholine, 1,2-diphytanoyl-sn-glycero-3-phosphoethanolamine (ME 16.0 PE), 1,2-distearoyl-sn-glycero-3-phosphoethanolamine, 1,2-dilinoleoyl-sn-glycero-3-phosphoethanolamine, 1,2-dilinolenoyl-sn-glycero-3-phosphoethanolamine, 1,2-diarachidonoyl-sn-glycero-3-phosphoethanolamine, 1,2-didocosahexaenoyl-sn-glycero-3-phosphoethanolamine, 1,2-dioleoyl-sn-glycero-3-phospho-rac-(1-glycerol) sodium salt (DOPG), sphingomyelin, and mixtures thereof;
the structural lipid is selected from the group consisting of cholesterol, fecosterol, sitosterol, ergosterol, campesterol, stigmasterol, brassicasterol, tomatidine, ursolic acid, alpha-tocopherol, and mixtures thereof; and/or
the PEG lipid is selected from the group consisting of a PEG-modified phosphatidylethanolamine, a PEG-modified phosphatidic acid, a PEG-modified ceramide, a PEG-modified dialkylamine, a PEG-modified diacylglycerol, a PEG-modified dialkylglycerol, and mixtures thereof.

Embodiment 31. The method of embodiment 28, wherein the lipid component further comprises a phospholipid that is DSPC, a structural lipid that is cholesterol, and/or a PEG lipid that is PEG-DMG.

Embodiment 32. The method according to any one of embodiments 28-31, wherein the N:P ratio of the nanoparticle is from about 2:1 to about 30:1.

Embodiment 33. The method of embodiment 32, wherein the N:P ratio of the nanoparticle is about 5.67:1.

Embodiment 34. The method of embodiment 32, wherein the N:P ratio of the nanoparticle is about 3:1.

Embodiment 35. The method according to any one of embodiments 28-34, wherein the wt/wt ratio of the lipid component to the modified RNA is from about 10:1 to about 100:1.

Embodiment 36. The method of embodiment 35, wherein the wt/wt ratio of the lipid component to the modified RNA is about 20:1.

Embodiment 37. The method of embodiment 35, wherein the wt/wt ratio of the lipid component to the modified RNA is about 10:1.

Embodiment 38. The method according to any one of embodiments 28-37, wherein the nanoparticle has a mean diameter from about 70 nm to about 80 nm.

Embodiment 39. The method of embodiment 38, wherein the nanoparticle has a mean diameter of about 72 nm.

Embodiment 40. The method according to any one of embodiments 28-39, wherein the administration results in a maximum observed plasma and/or tissue concentration, $C_{max}$, of the VEGF-A polypeptide of SEQ ID NO: 2 up to about 450 pg/ml plasma or pg/mg tissue.

Embodiment 41. The method according to any one of embodiments 28-39, wherein the administration results in a plasma and/or tissue total area under the concentration curve, $AUC_{0-t}$, of the VEGF-A polypeptide of SEQ ID NO: 2 up to about 5,500 pg*h/ml plasma or pg*h/mg tissue.

Embodiment 42. The method according to any one of embodiments 28-39, wherein the administration results in the production of more than about 400 pg/mg tissue of the VEGF-A polypeptide of SEQ ID NO: 2 within 8 hours.

Embodiment 43. The method according to any one of embodiments 28-39, wherein the administration results in the production of more than about 1 pg/mg tissue of the VEGF-A polypeptide of SEQ ID NO: 2 for up to 6 days.

Embodiment 44. The method according to any one of embodiments 28-39, wherein the nanoparticle or the pharmaceutical composition is administered intradermally.

Embodiment 45. The method according to any one of embodiments 28-39, wherein the concentration of the modified RNA is from about 0.01 mg/kg to about 10 mg/kg.

Embodiment 46. The method according to any one of embodiments 28-39, wherein the administration results in an increase of the production of the VEGF-A polypeptide of SEQ ID NO: 2 by a factor of about 5 to about 100, when compared to an administration of the modified RNA in a citrate saline buffer.

Embodiment 47. The method according to any one of embodiments 28-39, wherein the subject suffers from diabetes.

Embodiment 48. The method according to any one of embodiments 28-39, wherein the wound is a surgical wound, a burn, an abrasive wound, a skin biopsy site, a chronic wound, an injury (e.g., a traumatic injury wound), a graft wound, a diabetic wound, a diabetic ulcer (e.g., diabetic foot ulcer), a pressure ulcer, bed sore, and combinations thereof.

Embodiment 49. The method according to any one of embodiments 28-39, wherein the pharmaceutical composition comprises a pharmaceutically acceptable excipient, preferably a solvent, dispersion media, diluent, dispersion, suspension aid, surface active agent, isotonic agent, thickening or emulsifying agent, preservative, polymer, peptide, protein, cell, hyaluronidase, and mixtures thereof.

Embodiment 50. A method for inducing neovascularization in a mammalian tissue or a subject comprising administering to the mammalian tissue or subject an effective amount of the nanoparticle according to any one of embodiments 1-11 or the pharmaceutical composition according to any one of embodiments 12-27.

Embodiment 51. A method for inducing angiogenesis in a mammalian tissue or a subject comprising administering to the mammalian tissue or subject an effective amount of the nanoparticle according to any one of embodiments 1-11 or the pharmaceutical composition according to any one of embodiments 12-27.

Embodiment 52. A method for increasing capillary and/or arteriole density in a mammalian tissue or a subject comprising administering to the mammalian tissue or subject an effective amount of the nanoparticle according to any one of embodiments 1-11 or the pharmaceutical composition according to any one of embodiments 12-27.

6. DESCRIPTION OF DRAWINGS

Those of skill in the art will understand that the drawings, described below, are for illustrative purposes only. The drawings are not intended to limit the scope of the present teachings in any way.

FIG. 1: FIG. 1 shows the lipid compound (Compound A) used in the Examples.

FIGS. 2A and 2B: A diagram of the structure (FIG. 2A) of a modified VEGF-A RNA construct and the sequence (SEQ ID NO: 1, FIG. 2B) of a representative VEGF-A modified RNA.

Figure 3:
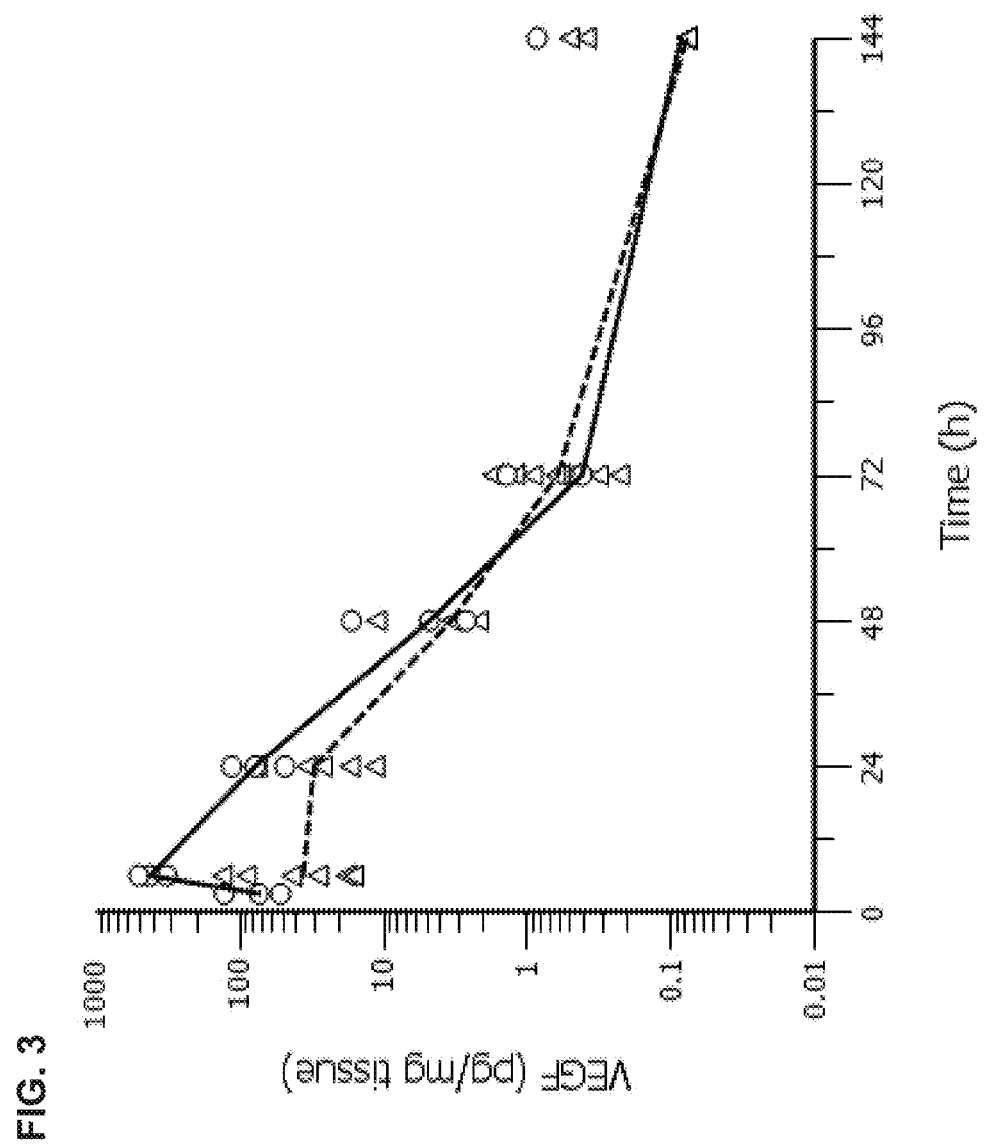

FIG. 3: Human VEGF-A protein content in skin biopsies as a function of time up to 144 hours after intradermal injection of 100 μg VEGF-A modified RNA formulated in citrate saline (triangles, dashed line) and 3 μg VEGF-A modified RNA formulated in lipid nanoparticles (LNP) (circles, solid line), respectively. The lines represent the median at each time point.

Figure 4:
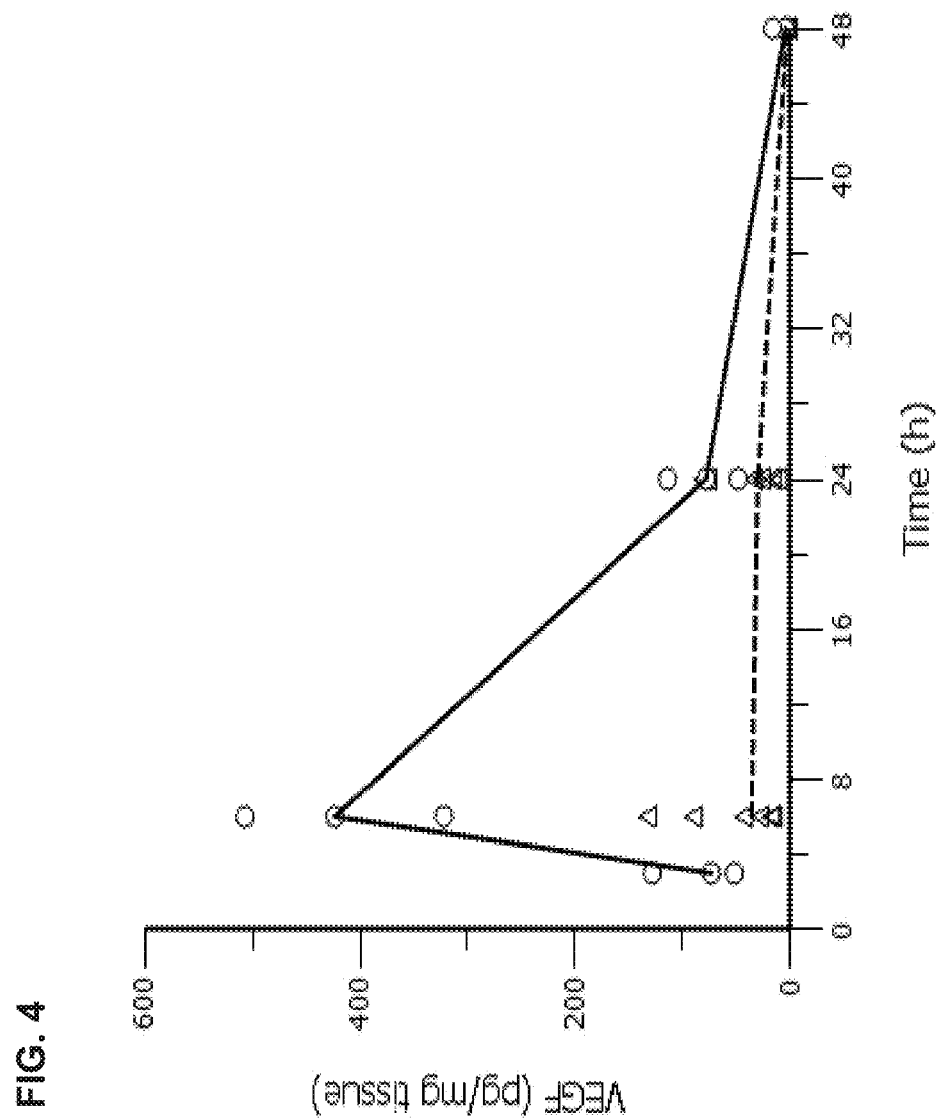

FIG. 4: Human VEGF-A protein content in skin biopsies as a function of time up to 48 hours after intradermal injection of 100 μg VEGF-A modified RNA formulated in citrate saline (triangles, dashed line) and 3 μg VEGF-A modified RNA formulated in LNP (circles, solid line), respectively. The lines represent the median at each time point.

Figure 5:
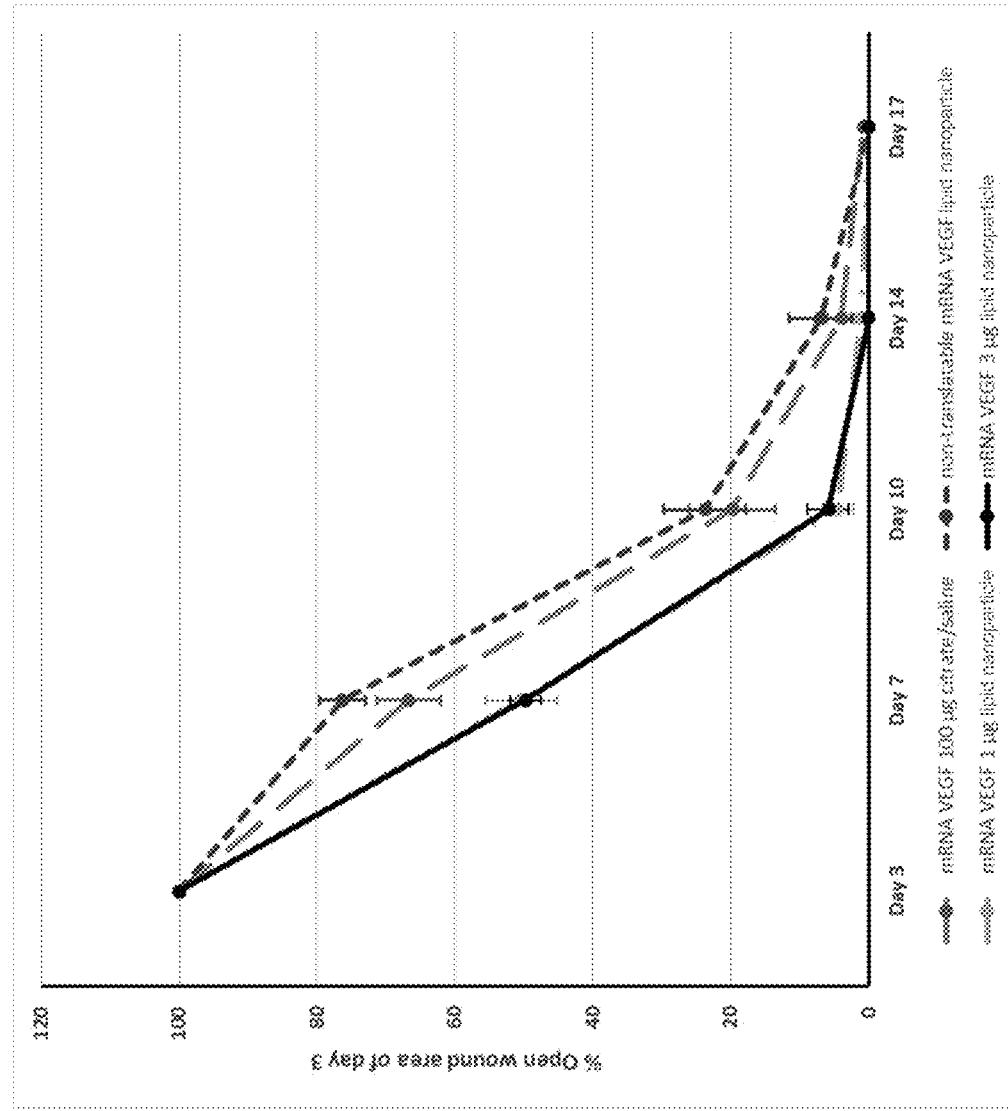

FIG. 5: Percent wound healing following intradermal injections of the following compositions: (1) a lipid nanoparticle composition comprising 1 μg VEGF-A modified RNA (n=6), (2) a lipid nanoparticle composition comprising 3 μg VEGF-A modified RNA (n=6), (3) a lipid nanoparticle composition comprising 3 μg non-translatable VEGF-A RNA (n=6), and (4) a citrate saline composition comprising 100 μg VEGF-A modified RNA (n=7).

Figure 6:
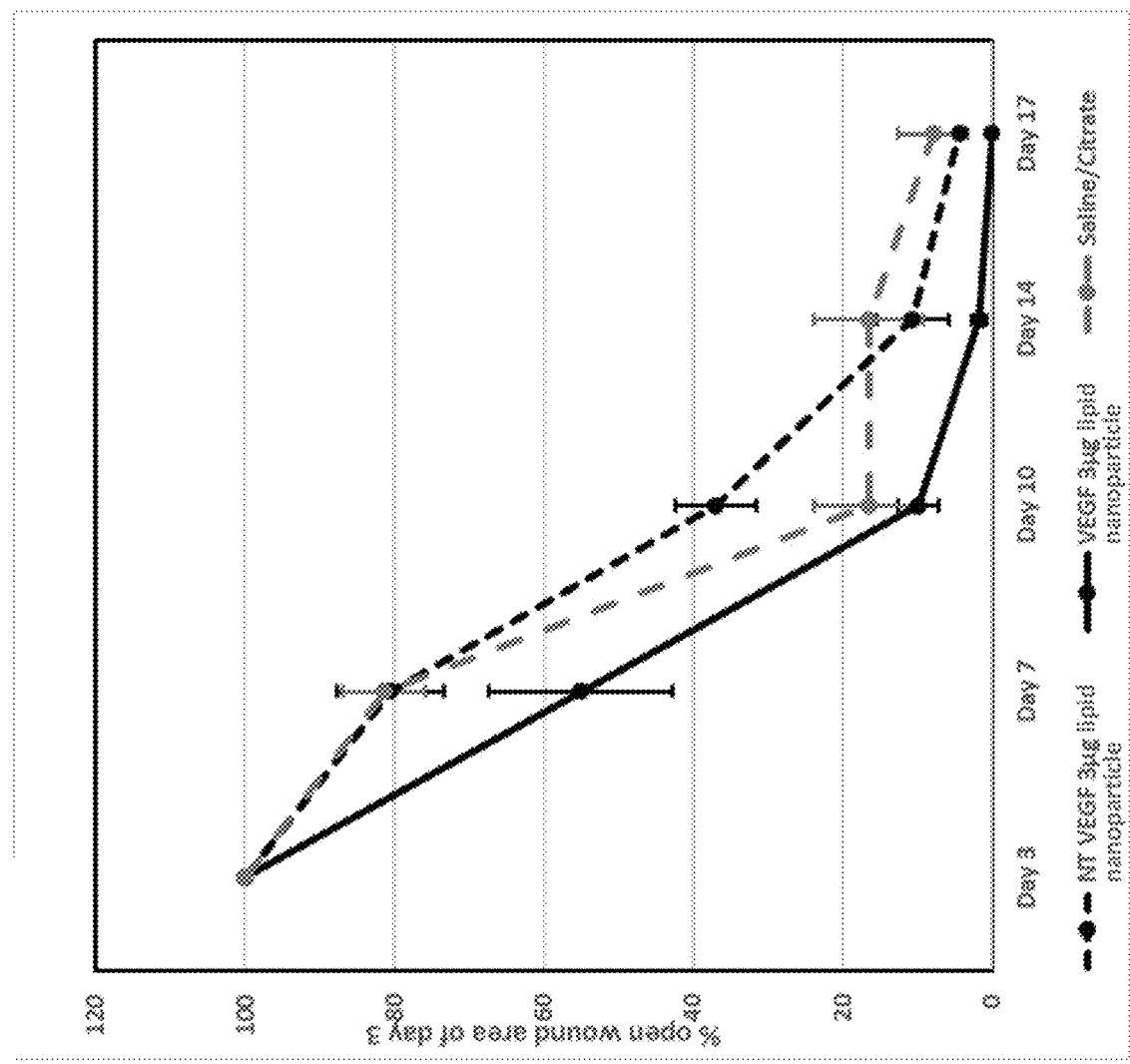

FIG. 6: Percent wound healing following intradermal injections of the following compositions: (1) a lipid nanoparticle composition comprising 3 μg VEGF-A modified RNA (n=5), (2) a lipid nanoparticle composition comprising 3 μg non-translatable VEGF-A modified RNA (n=5), and (3) a citrate saline composition that does not comprise any modified RNA (n=5).

Figure 7:
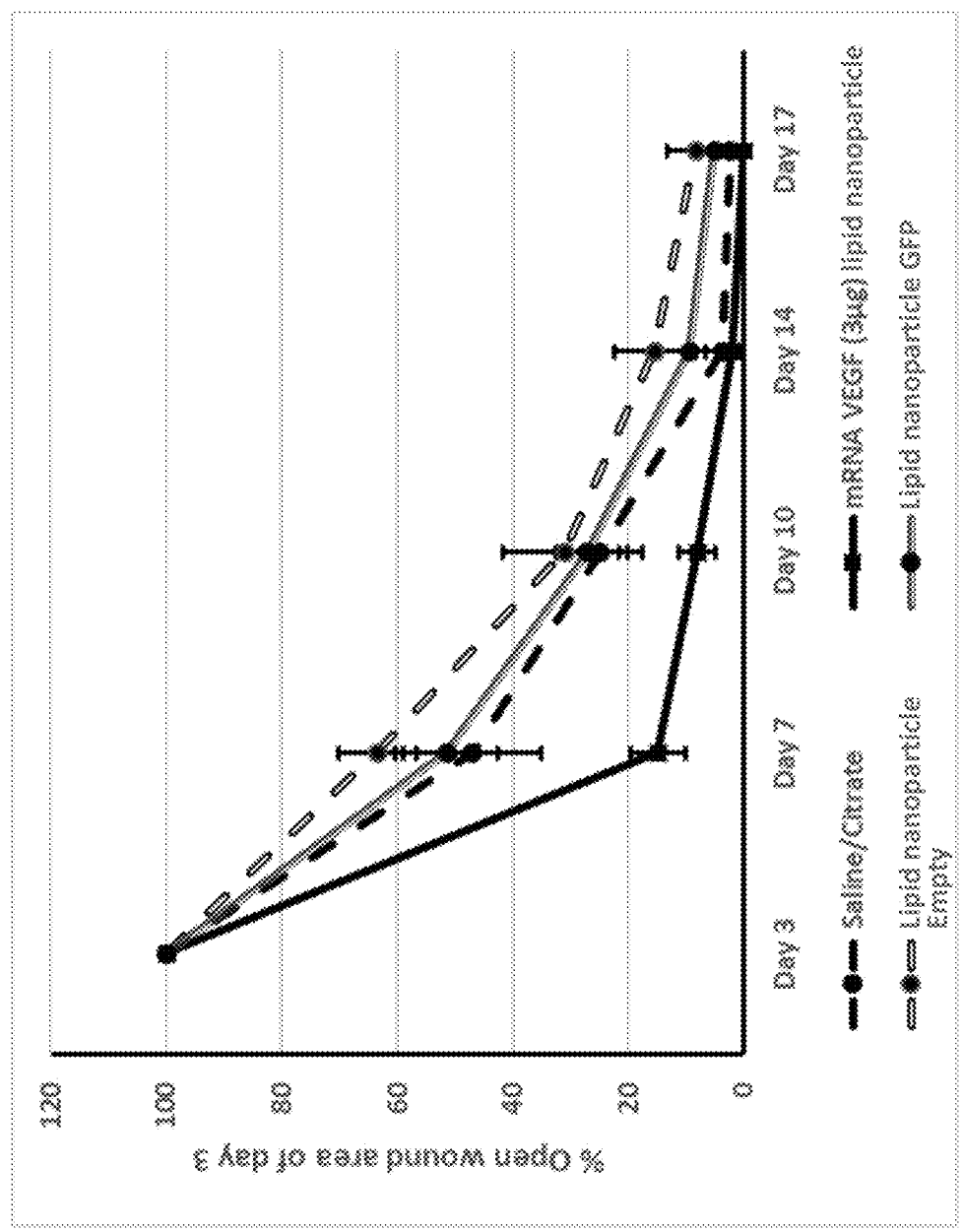

FIG. 7: Percent wound healing following intradermal injections of the following compositions: (1) a lipid nanoparticle composition comprising 3 μg VEGF-A modified RNA (n=6), (2) a lipid nanoparticle composition that does not comprise any modified RNA (n=5), (3) a lipid nanoparticle composition comprising 3 μg GFP modified RNA (n=6), and (4) a citrate saline composition that does not comprise any modified RNA (n=6).

Figure 8:
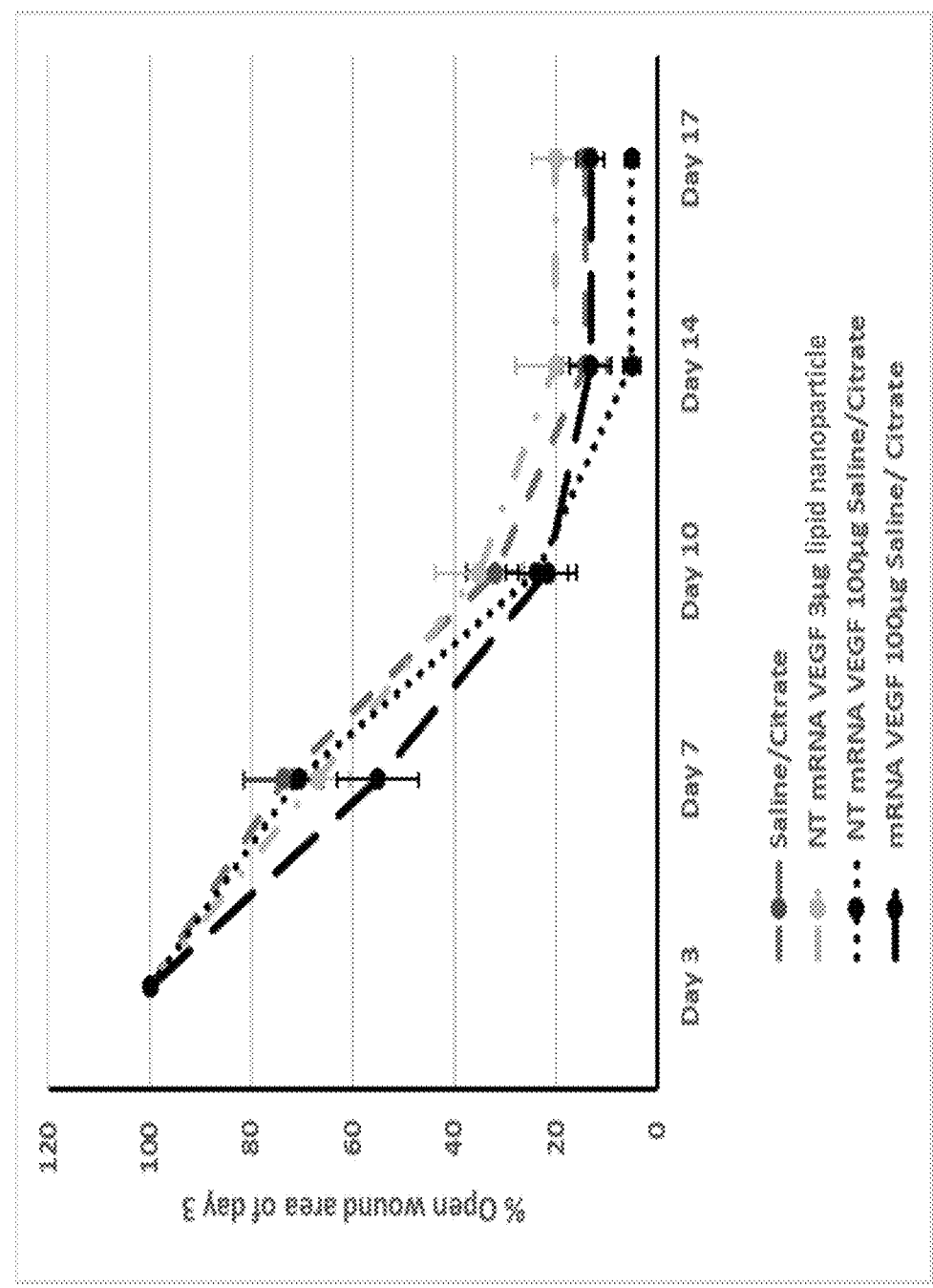

FIG. 8: Percent wound healing following intradermal injections of the following compositions: (1) a lipid nanoparticle composition comprising 3 μg non-translatable VEGF-A modified RNA (n=7), (2) a citrate saline composition comprising 100 μg VEGF-A modified RNA (n=7), (3) a citrate saline composition comprising 100 μg non-trans-latable VEGF-A modified RNA (n=7), and (4) a citrate saline composition that does not comprise any modified RNA (n=7).

7. DETAILED DESCRIPTION

All references referred to in this disclosure are incorporated herein by reference in their entireties.

Many modifications and other embodiments of the disclosures set forth herein will come to mind to one skilled in the art to which these disclosures pertain having the benefit of the teachings presented in the foregoing descriptions and the associated drawings. Therefore, it is to be understood that the disclosures are not to be limited to the specific embodiments disclosed and that modifications and other embodiments are intended to be included within the scope of the appended claims. Although specific terms are employed herein, they are used in a generic and descriptive sense only and not for purposes of limitation.

Units, prefixes and symbols may be denoted in their SI accepted form. Unless otherwise indicated, nucleic acids are written left to right in 5' to 3' orientation; amino acid sequences are written left to right in amino to carboxy orientation, respectively. Numeric ranges are inclusive of the numbers defining the range. The recitation of ranges of values herein is merely intended to serve as a shorthand method of referring individually to each separate value falling within the range. Unless otherwise indicated herein, each individual value is incorporated into the specification as if it were individually recited herein. Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

7.1. Definitions

Unless specifically defined otherwise, all technical and scientific terms used herein have the same meaning as commonly understood by one of ordinary skill in the art to which this disclosure belongs. Unless mentioned otherwise, the techniques employed or contemplated herein are standard methodologies well known to one of ordinary skill in the art. The practice of the present disclosure will employ, unless otherwise indicated, conventional techniques of microbiology, tissue culture, molecular biology, chemistry, biochemistry and recombinant DNA technology, which are within the skill of the art. The materials, methods and examples are illustrative only and not limiting. The following is presented by way of illustration and is not intended to limit the scope of the disclosure.

In some embodiments, the numerical parameters set forth in the specification (into which the claims are incorporated in their entirety) are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the present disclosure are approximations, the numerical values set forth in the specific examples are reported as precisely as practicable. The numerical values presented in some embodiments of the present disclosure may contain certain errors necessarily resulting from the standard deviation found in their respective testing measurements. The recitation of ranges of values herein is merely intended to serve as a shorthand method of referring individually to each separate value falling within the range. Unless otherwise indicated herein, each individual value is incorporated into the specification as if it were individually recited herein.

For convenience, certain terms employed in the entire application (including the specification, examples, and appended claims) are collected here. Unless defined otherwise, all technical and scientific terms used herein have the same meaning as commonly understood by one of ordinary skill in the art to which this disclosure belongs.

In some embodiments, numbers expressing quantities of ingredients, properties such as molecular weight, reaction conditions and results, and so forth, used to describe and claim certain embodiments of the present disclosure are to be understood as being modified in some instances by the term "about." One of ordinary skill in the art would understand the meaning of the term "about" in the context of the value that it qualifies. In some embodiments, the term "about" is used to indicate that a value includes the standard deviation of the mean for the device or method being employed to determine the value. In some embodiments, the numerical parameters set forth in the specification (into which the claims are incorporated in their entirety) are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the present disclosure are approximations, the numerical values set forth in the specific examples are reported as precisely as practicable. The numerical values presented in some embodiments of the present disclosure may contain certain errors necessarily resulting from the standard deviation found in their respective testing measurements.

As used herein, the term "administering" refers to the placement of a nanoparticle and/or a pharmaceutical composition comprising at least one nanoparticle into a mammalian tissue or a subject by a method or route that results in at least partial localization of the nanoparticle and/or composition at a desired site or tissue location. In some embodiments, nanoparticles comprising a lipid component and a modified RNA can be administered via an intradermal route. In some embodiments, at least a portion of the protein expressed by the modified RNA is localized to a desired target tissue or target cell location via intradermal administration.

The term "pharmaceutical composition" refers to a mixture that contains a therapeutically active component(s) and a carrier or excipient, such as a pharmaceutically acceptable carrier or excipient that is conventional in the art. For example, a pharmaceutical composition as used herein usually comprises at least a lipid component, a modified RNA according to the disclosure, and a suitable excipient.

The term "compound" includes all isotopes and isomers of the structure depicted. "Isotope" refers to atoms having the same atomic number but different mass numbers resulting from a different number of neutrons in the nuclei. For example, isotopes of hydrogen include tritium and deuterium. Further, a compound, salt, or complex of the present disclosure can be prepared in combination with solvent or water molecules to form solvates and hydrates by routine methods. "Isomer" means any geometric isomer, tautomer, zwitterion, stereoisomer, enantiomer, or diastereomer of a compound. Compounds may include one or more chiral centers and/or double bonds and may thus exist as stereoisomers, such as double-bond isomers or diastereomers. The present disclosure encompasses any and all isomers of the compounds described herein, including stereomerically pure forms and enantiomeric and stereoisomeric mixtures, e.g., racemates. Enantiomeric and stereometric mixtures of compounds and means of resolving them into their component enantiomers or stereoisomers are well-known in the art.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and can also cover other unlisted steps. Similarly, any composition that "comprises," "has" or "includes" one or more features is not limited to possessing only those one or more features and can cover other unlisted features. The use of any and all examples, or exemplary language (e.g. "such as") provided with respect to certain embodiments herein is intended merely to better illuminate the present disclosure and does not pose a limitation on the scope of the present disclosure otherwise claimed. No language in the specification should be construed as indicating any non-claimed element as essential to the practice of the present disclosure.

The term "consisting essentially of" allows for the presence of additional materials or steps that "do not materially affect the basic and novel characteristic(s)" of the claimed invention.

The term "consisting of" refers to compositions, methods, and respective components thereof as described herein, which are exclusive of any element not recited in that description of the embodiment.

The term "delivering" means providing an entity to a destination. For example, delivering a therapeutic to a subject may involve administering a pharmaceutical composition comprising at least one nanoparticle including the modified RNA to the subject (e.g., by an intradermal route). Administration of a pharmaceutical composition comprising at least one nanoparticle to mammalian tissue or a subject may involve contacting one or more cells with the pharmaceutical composition.

The terms "disease" or "disorder" are used interchangeably herein, and refers to any alternation in state of the body or of some of the organs, interrupting or disturbing the performance of the functions and/or causing symptoms such as discomfort, dysfunction, distress, or even death to the person afflicted or those in contact with a person. A disease or disorder can also related to a distemper, ailing, ailment, malady, sickness, illness, complaint, indisposition, or affection.

The term "effective amount" as used herein refers to the amount of therapeutic agent (for example, a modified RNA) or pharmaceutical composition sufficient to reduce at least one or more symptom(s) of the disease or disorder, or to provide the desired effect. For example, it can be the amount that induces a therapeutically significant reduction in a symptom or clinical marker associated with wound healing.

As used herein, "expression" of a nucleic acid sequence refers to one or more of the following events: (1) production of an RNA template from a DNA sequence (e.g., by transcription); (2) processing of an RNA transcript (e.g., by splicing, editing, 5' cap formation, and/or 3' end processing);

(3) translation of an RNA into a polypeptide or protein; and (4) post-translational modification of a polypeptide or protein.

As used herein, the term "lipid component" is that component of a nanoparticle that includes one or more lipids. For example, the lipid component may include one or more cationic/ionizable, PEGylated, structural, or other lipids, such as phospholipids. In one embodiment, the lipid component comprises Compound A (FIG. 1).

As used herein, the term "modified RNA" refers to RNA molecules containing one, two, or more than two nucleoside modifications comparing to adenosine (A) ((2R,3R,4S,5R)-2-(6-amino-9H-purin-9-yl)-5-(hydroxymethyl)oxolane-3,4-diol), guanosine (G) (2-Amino-9-[3,4-dihydroxy-5-(hydroxymethyl)oxolan-2-yl]-3H-purin-6-one), cytidine (C) (4-amino-1-[3,4-dihydroxy-5-(hydroxymethyl) tetrahydrofuran-2-yl]pyrimidin-2-one), and uridine (U) (1-[(3R,4S,5R)-3,4-dihydroxy-5-(hydroxymethyl)oxolan-2-yl]pyrimidine-2,4-dione), or compared to AMP, GMP, CMP, and UMP, in RNA molecules, or a portion thereof. Non-limiting examples of nucleoside modifications are provided elsewhere in this specification. Where the nucleotide sequence of a particular claimed RNA is otherwise identical to the sequence of a naturally-existing RNA molecule, the modified RNA is understood to be an RNA molecule with at least one modification different from those existing in the natural counterpart. The difference can be either in the chemical change to the nucleoside/nucleotide or in the position of that change within the sequence. In one embodiment, the modified RNA is a modified messenger RNA (or "modified mRNA"). In some embodiments, a modified RNA includes at least one UMP that is modified to form N1-methyl-pseudo-UMP. In some embodiments, all UMPs in a modified RNA have been replaced by N1-methyl-pseudo-UMP.

As used herein, a "nanoparticle" is a particle comprising one or more lipids and one or more therapeutic agents. Nanoparticles are typically sized on the order of micrometers or smaller and may include a lipid bilayer. In some embodiments, the nanoparticle has a mean diameter (e.g., a hydrodynamic diameter) of between about 50 nm and about 100 nm, for example between about 60 nm and about 90 nm, between 70 nm and 80 nm in diameter, as measured by dynamic light scattering (see NIST Special Publication 1200-6, "Measuring the Size of Nanoparticles in Aqueous Media Using Batch Mode Dynamic Light Scattering"). In some embodiments, the nanoparticle has a mean hydrodynamic diameter of about 71 nm, 72 nm, 73 nm, 74 nm, 75 nm, 76 nm, 77 nm, 78 nm, 79 nm, 80 nm, 81 nm, 82 nm, 83 nm, 84 nm, 85 nm, 86 nm, 87 nm, 88 nm, 89 nm or 90 nm. In some embodiments, the therapeutic agent is a modified RNA. In some embodiments, the nanoparticles comprise Compound A as shown in FIG. 1 and a modified RNA.

As used herein, the "polydispersion index (pDI)" is the measure of the distribution of nanoparticle sizes in a nanoparticulate sample (see NIST Special Publication 1200-6, "Measuring the Size of Nanoparticles in Aqueous Media Using Batch Mode Dynamic Light Scattering"). In some embodiments, the polydispersity index is between about 0.10 and about 0.20, for example, about 0.10, 0.11, 0.12, 0.13, 0.14, 0.15, 0.16, 0.17, 0.18, 0.19 or 0.20.

As used herein, the "N:P ratio" is the molar ratio of ionizable (in the physiological pH range) nitrogen atoms in a lipid to phosphate groups in an RNA, e.g., in a nanoparticle including a lipid component and a modified RNA.

As used herein, the term "nucleic acid," in its broadest sense, includes any compound and/or substance that comprises a polymer of nucleotides linked via a phosphodiester bond. These polymers are often referred to as oligonucleotides or polynucleotides, depending on the size. The terms "polynucleotide sequence" and "nucleotide sequence" are also used interchangeably herein.

As used herein, a "PEG lipid" or "PEGylated lipid" refers to a lipid comprising a polyethylene glycol component.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. Drug-approval agencies (e.g., EMA, US-FDA) provide guidance and approve pharmaceutically acceptable compounds, materials, compositions, and/or dosage forms. Examples are listed in Pharmacopeias.

The phrase "pharmaceutically acceptable excipient" is employed herein to refer to a pharmaceutically acceptable material chosen from a solvent, dispersion media, diluent, dispersion, suspension aid, surface active agent, isotonic agent, thickening or emulsifying agent, preservative, polymer, peptide, protein, cell, hyaluronidase, and mixtures thereof. In some embodiments, the solvent is an aqueous solvent.

As used herein, a "phospholipid" is a lipid that includes a phosphate moiety and one or more carbon chains, such as unsaturated fatty acid chains. A phospholipid may include one or more multiple (e.g., double or triple) bonds (e.g., one or more unsaturations). Particular phospholipids may facilitate fusion to a membrane. For example, a cationic phospholipid may interact with one or more negatively charged phospholipids of a membrane (e.g., a cellular or intracellular membrane). Fusion of a phospholipid to a membrane may allow one or more elements of a lipid-containing composition to pass through the membrane permitting, e.g., delivery of the one or more elements to a cell.

As used herein, "polypeptide" means a polymer of amino acid residues (natural or unnatural) linked together most often by peptide bonds. The term, as used herein, refers to proteins, polypeptides, and peptides of any size, structure, or function. A polypeptide may be a single molecule or may be a multi-molecular complex such as a dimer, trimer or tetramer. They may also comprise single chain or multichain polypeptides such as antibodies or insulin and may be associated or linked. Most commonly disulfide linkages are found in multichain polypeptides. The term polypeptide may also apply to amino acid polymers in which one or more amino acid residues are an artificial chemical analogue of a corresponding naturally occurring amino acid.

As used herein, "protein" is a polymer consisting essentially of any of the 20 amino acids. Although "polypeptide" is often used in reference to relatively large polypeptides, and "peptide" is often used in reference to small polypeptides, usage of these terms in the art overlaps and is varied. The terms "peptide(s)", "protein(s)" and "polypeptide(s)" are sometime used interchangeably herein.

The term "subject" refers to an animal, for example a human, to whom treatment, including prophylactic treatment, with methods and compositions described herein, is provided. For treatment of those conditions or disease states which are specific for a specific animal such as a human subject, the term "subject" refers to that specific animal.

The term "tissue" refers to a group or layer of similarly specialized cells which together perform certain special functions.

As used herein, the terms "treat," "treatment," or "treating" refers to an amelioration or elimination of a disease or disorder, or at least one discernible symptom thereof. In some embodiments, "treatment" or "treating" refers to an amelioration or elimination of at least one measurable physical parameter, not necessarily discernible by the patient.

It should be understood that this disclosure is not limited to the particular methodology, protocols, and reagents, etc., described herein and as such can vary. The terminology used herein is for the purpose of describing particular embodiments only, and is not intended to limit the scope of the present disclosure, which is defined solely by the claims.

7.2. Lipid Components

Nanoparticles comprise a lipid component including Compound A (FIG. 1). Additional compounds are disclosed in WO 2017/049245 A2 (see, e.g., compounds 1-147 in WO 2017/049245 A2), which is incorporated herein by reference in its entirety. The lipid components may also include a variety of other lipids such as a phospholipid, a structural lipid, and/or a PEG lipid.

Phospholipids

The lipid component of a nanoparticle may include one or more phospholipids, such as one or more (poly)unsaturated lipids. Phospholipids may assemble into one or more lipid bilayers. In general, phospholipids may include a phospholipid moiety and one or more fatty acid moieties.

Phospholipids useful in the compositions and methods may be selected from the non-limiting group consisting of 1,2-distearoyl-sn-glycero-3-phosphocholine (DSPC), 1,2-dioleoyl-sn-glycero-3-phosphoethanolamine (DOPE), 1,2-dilinoleoyl-sn-glycero-3-phosphocholine (DLPC), 1,2-dimyristoyl-sn-gly cero-phosphocholine (DMPC), 1,2-dioleoyl-sn-glycero-3-phosphocholine (DOPC), 1,2-dipalmitoyl-sn-glycero-3-phosphocholine (DPPC), 1,2-diundecanoyl-sn-glycero-phosphocholine (DUPC), 1-palmitoyl-2-oleoyl-sn-glycero-3-phosphocholine (POPC), 1,2-di-O-octadecenyl-sn-glycero-3-phosphocholine (18:0 Diether PC), 1-oleoyl-2-cholesterylhemisuccinoyl-sn-glycero-3-phosphocholine (OChemsPC), 1-hexadecyl-sn-glycero-3-phosphocholine (C16 Lyso PC), 1,2-dilinolenoyl-sn-glycero-3-phosphocholine, 1,2-diarachidonoyl-sn-glycero-3-phosphocholine, 1,2-didocosahexaenoyl-sn-glycero-3-phosphocholine, 1,2-diphytanoyl-sn-glycero-3-phosphoethanolamine (ME 16.0 PE), 1,2-distearoyl-sn-glycero-3-phosphoethanolamine, 1,2-dilinoleoyl-sn-glycero-3-phosphoethanolamine, 1,2-dilinolenoyl-sn-glycero-3-phosphoethanolamine, 1,2-diarachidonoyl-sn-glycero-3-phosphoethanolamine, 1,2-didocosahexaenoyl-sn-glycero-3-phosphoethanolamine, 1,2-dioleoyl-sn-glycero-3-phospho-rac-(1-glycerol) sodium salt (DOPG), and sphingomyelin. In some embodiments, a lipid component includes DSPC. In some embodiments, a lipid component includes DOPE. In some embodiments, a lipid component includes both DSPC and DOPE.

Structural Lipids

The lipid component of a nanoparticle may include one or more structural lipids. Structural lipids can be selected from, but are not limited to, cholesterol, fecosterol, sitosterol, ergosterol, campesterol, stigmasterol, brassicasterol, tomatidine, tomatine, ursolic acid, alpha-tocopherol, and mixtures thereof. In some embodiments, the structural lipid is cholesterol. In some embodiments, the structural lipid includes cholesterol and a corticosteroid (such as prednisolone, dexamethasone, prednisone, and hydrocortisone), or a combination thereof. In some embodiments, a lipid component includes cholesterol.

PEG Lipids

The lipid component of a nanoparticle may include one or more PEG or PEG-modified lipids. Such lipids may be alternately referred to as PEGylated lipids. A PEG lipid is a lipid modified with polyethylene glycol. A PEG lipid may be selected from the non-limiting group consisting of PEG-modified phosphatidylethanolamines, PEG-modified phosphatidic acids, PEG-modified ceramides, PEG-modified dialkylamines, PEG-modified diacylglycerols, PEG-modified dialkylglycerols, and mixtures thereof. For example, a PEG lipid may be PEG-c-DOMG, PEG-DMG (1,2-dimyristoyl-OT-glycerol methoxypoly ethylene glycol, obtainable from Avanti Polar Lipids, Alabaster, AL), PEG-DLPE, PEG-DMPE, PEG-DPPC, or a PEG-DSPE lipid. In some embodiments, a lipid component includes PEG-DMG.

7.3. Modified RNAs Encoding VEGF-A Polypeptides

It is of great interest in the fields of therapeutics, diagnostics, reagents and for biological assays to be able to deliver a nucleic acid, e.g., a ribonucleic acid (RNA) inside a cell, whether in vitro, in vivo, in situ, or ex vivo, such as to cause intracellular translation of the nucleic acid and production of an encoded polypeptide of interest.

Naturally occurring RNAs are synthesized from four basic ribonucleotides: ATP, CTP, UTP and GTP, but may contain post-transcriptionally modified nucleotides. Further, approximately one hundred different nucleoside modifications have been identified in RNA (Rozenski, J, Crain, P, and McCloskey, J., The RNA Modification Database: 1999 update, Nucl Acids Res, (1999) 27: 196-197).

According to the present disclosure, these RNAs are preferably modified as to avoid the deficiencies of other RNA molecules of the art (e.g., activating the innate immune response and rapid degradation upon administration). Hence, these polynucleotides are referred to as modified RNA. In some embodiments, the modified RNA avoids the innate immune response upon administration to a subject. In some embodiments, the half-life of the modified RNA is extended compared to an unmodified RNA.

In preferred embodiments, the RNA molecule is a messenger RNA (mRNA). As used herein, the term "messenger RNA" (mRNA) refers to any polynucleotide that encodes a polypeptide of interest and that is capable of being translated to produce the encoded polypeptide of interest in vitro, in vivo, in situ or ex vivo.

As depicted in FIG. 2A, traditionally, the basic components of an mRNA molecule include at least a coding region, a 5' untranslated region (UTR), a 3' untranslated region (UTR), a 5' cap and a poly-(A) tail. Building on this wild-type modular structure, the present disclosure expands the scope of functionality of traditional mRNA molecules by providing polynucleotides or primary RNA constructs which maintain a modular organization, but which comprise one or more structural and/or chemical modifications or alterations that impart useful properties to the polynucleotide including, in some embodiments, the lack of a substantial induction of the innate immune response of a cell into which the polynucleotide is introduced.

The modified RNAs can include any useful modification relative to the standard RNA nucleotide chain, such as to the sugar, the nucleobase (e.g., one or more modifications of a nucleobase, such as by replacing or substituting an atom of a pyrimidine nucleobase with optionally substituted amino, optionally substituted thiol, optionally substituted alkyl (e.g., methyl or ethyl), or halo (e.g., chloro or fluoro)), or the internucleoside linkage (e.g., one or more modification to the phosphodiester backbone).

As non-limiting examples, in some embodiments, a modified RNA can include, for example, at least one uridine monophosphate (UMP) that is modified to form N1-methyl-pseudo-UMP. In some embodiments, the N1-methyl-pseudo-UMP is present instead of UMP in a percentage of the UMPs in the sequence of 0.1%, 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, 99.9%, and 100%. In some embodiments, all UMP have been replaced by N1-methyl-pseudo-UMP.

In some embodiments, modified RNAs comprise a modification to 5' cap, such as a 5' diguanosine cap. In some embodiments, modified RNAs comprise a modification to a coding region. In some embodiments, modified RNAs comprise a modification to a 5' UTR. In some embodiments, modified RNAs comprise a modification to a 3' UTR. In some embodiments, modified RNAs comprise a modification to a poly-(A) tail. In some embodiments, modified RNAs comprise any combination of modifications to a coding region, 5' cap, 5' UTR, 3' UTR, or poly-(A) tail. In some embodiments, a modified RNA can optionally be treated with an alkaline phosphatase.

In some embodiments, a modified RNA encodes a Vascular Endothelial Growth Factor (VEGF) polypeptide, any one of a large family of VEGF proteins that play a central role in the regulation of wound healing in general. VEGF's roles also include activation of nitric oxide (NO) signaling, developmental and post-natal angiogenesis, tumor angiogenesis, arteriogenesis, endothelial replication, and as cell fate switch for multipotent cardiovascular progenitors.

It will be appreciated by those of skill in the art that for any particular VEGF gene there may exist one or more variants or isoforms. Non-limiting examples of VEGF-A polypeptides in accordance with the present disclosure are listed in Table 1. It will be appreciated by those of skill in the art that the sequences disclosed in Table 1 contain potential flanking regions. These are encoded in each nucleotide sequence either to the 5' (upstream) or 3' (downstream) of the open reading frame. The open reading frame is definitively and specifically disclosed by teaching the nucleotide reference sequence. It is also possible to further characterize the 5' and 3' flanking regions by utilizing one or more available databases or algorithms. Databases have annotated the features contained in the flanking regions of the NCBI sequences and these are available in the art.

TABLE 1

*Homo sapiens* VEGF-A mRNA isoforms.

| Description | NM Ref. | NP Ref. |
| --- | --- | --- |
| *Homo sapiens* vascular endothelial growth factor A (VEGF-A), transcript variant 1, mRNA | NM_001171623.1 | NP_001165094.1 |
| *Homo sapiens* vascular endothelial growth factor A (VEGF-A), transcript variant 1, mRNA | NM_001025366.2 | NP_001020537.2 |
| *Homo sapiens* vascular endothelial growth factor A (VEGF-A), transcript variant 2, mRNA | NM_001171624.1 | NP_001165095.1 |
| *Homo sapiens* vascular endothelial growth factor A (VEGF-A), transcript variant 2, mRNA | NM_003376.5 | NP_003367.4 |
| *Homo sapiens* vascular endothelial growth factor A (VEGF-A), transcript variant 3, mRNA | NM_001171625.1 | NP_001165096.1 |
| *Homo sapiens* vascular endothelial growth factor A (VEGF-A), transcript variant 3, mRNA | NM_001025367.2 | NP_001020538.2 |
| *Homo sapiens* vascular endothelial growth factor A (VEGF-A), transcript variant 4, mRNA | NM_001171626.1 | NP_001165097.1 |
| *Homo sapiens* vascular endothelial growth factor A (VEGF-A), transcript variant 4, mRNA | NM_001025368.2 | NP_001020539.2 |
| *Homo sapiens* vascular endothelial growth factor A (VEGF-A), transcript variant 4, mRNA | NM_001317010.1 | NP_001303939.1 |
| *Homo sapiens* vascular endothelial growth factor A (VEGF-A), transcript variant 5, mRNA | NM_001171627.1 | NP_001165098.1 |
| *Homo sapiens* vascular endothelial growth factor A (VEGF-A), transcript variant 5, mRNA | NM_001025369.2 | NP_001020540.2 |
| *Homo sapiens* vascular endothelial growth factor A (VEGF-A), transcript variant 6, mRNA | NM_001171628.1 | NP_001165099.1 |
| *Homo sapiens* vascular endothelial growth factor A (VEGF-A), transcript variant 6, mRNA | NM_001025370.2 | NP_001020541.2 |
| *Homo sapiens* vascular endothelial growth factor A (VEGF-A), transcript variant 7, mRNA | NM_001171629.1 | NP_001165100.1 |

TABLE 1-continued

Homo sapiens VEGF-A mRNA isoforms.

| Description | NM Ref. | NP Ref. |
| --- | --- | --- |
| Homo sapiens vascular endothelial growth factor A (VEGF-A), transcript variant 7, mRNA | NM_001033756.2 | NP_001028928.1 |
| Homo sapiens vascular endothelial growth factor A (VEGF-A), transcript variant 8, mRNA | NM_001171630.1 | NP_001165101.1 |
| Homo sapiens vascular endothelial growth factor A (VEGF-A), transcript variant 8, mRNA | NM_001171622.1 | NP_001165093.1 |
| Homo sapiens vascular endothelial growth factor A (VEGF-A), transcript variant 9, mRNA | NM_001204385.1 | NP_001191314.1 |
| Homo sapiens vascular endothelial growth factor A (VEGF-A), transcript variant 9, mRNA | NM_001204384.1 | NP_001191313.1 |
| Homo sapiens vascular endothelial growth factor A (VEGF-A), transcript variant 10, mRNA | NM_001287044.1 | NP_001273973.1 |

It will be appreciated by those of skill in the art that RNA molecules encoding VEGF-A polypeptides, e.g., a human VEGF-A polypeptide, can be designed according to the VEGF-A mRNA isoforms listed in Table 1. One of ordinary of skill in the art is generally familiar with the multiple isoforms of the remaining VEGF family members.

In one embodiment, the present disclosure provides for a modified RNA encoding a VEGF-A polypeptide (e.g., SEQ ID NO: 2). In some embodiments, a modified RNA encodes a VEGF-A polypeptide, wherein the modified RNA comprises any one of SEQ ID NOs: 1 and 3-5. In some embodiments, the modified RNA further comprises a 5' cap, a 5' UTR, a 3' UTR, a poly(A) tail, or any combinations thereof. In some embodiments, the 5' cap, the 5' UTR, the 3' UTR, the poly(A) tail, or any combinations thereof may include one or more modified nucleotides.

In some embodiments, a modified RNA encoding a VEGF-A polypeptide can have the structure as depicted in FIG. 2B, which is SEQ ID NO: 1. In some embodiments, a modified RNA encoding a VEGF-A polypeptide can have the sequence of any one of SEQ ID NOs: 3-5.

7.4. Compositions Comprising Lipid Component and Modified RNA

Some embodiments relate to nanoparticles that include a lipid component and a modified RNA.

In some embodiments, the lipid component of a nanoparticle may include Compound A (FIG. 1). In some embodiments, the lipid component of a nanoparticle may further include a phospholipid, a structural lipid, and/or a PEG lipid as disclosed herein. For example, in some embodiments, the lipid component of a nanoparticle may include DSPC, cholesterol, PEG-DMG, and mixtures thereof.

The elements of the lipid component may be provided in specific fractions. In some embodiments, the lipid component of a nanoparticle includes Compound A, a phospholipid, a structural lipid, and a PEG lipid. In some embodiments, the lipid component of the nanoparticle includes from about 30 mol % to about 60 mol % Compound A, from about 0 mol % to about 30 mol % phospholipid, from about 18.5 mol % to about 48.5 mol % structural lipid, and from about 0 mol % to about 10 mol % of PEG lipid, provided that the total mol % does not exceed 100%. In some embodiments, the lipid component of the nanoparticle includes from about 35 mol % to about 55 mol % Compound A, from about 5 mol % to about 25 mol % phospholipid, from about 30 mol % to about 40 mol % structural lipid, and from about 0 mol % to about 10 mol % of PEG lipid. In some embodiment, the lipid component includes about 50 mol % Compound A, about 10 mol % phospholipid, about 38.5 mol % structural lipid, and about 1.5 mol % of PEG lipid. In some embodiments, the phospholipid may be DOPE. In some embodiments, the structural lipid may be cholesterol. In some embodiments, the PEG lipid may be PEG-DMG.

In some embodiments, the modified RNA component of a nanoparticle may include a modified RNA encoding a VEGF-A polypeptide as disclosed herein (e.g., SEQ ID NO: 2). In some embodiments, the modified RNA component of a nanoparticle may include the modified RNA comprises any one of SEQ ID NOs: 1 and 3-5. In some embodiments, the modified RNA further comprises a 5' cap, a 5' UTR, a 3' UTR, a poly(A) tail, or any combinations thereof. In some embodiments, the 5' cap, the 5' UTR, the 3' UTR, the poly(A) tail, or any combinations thereof may include one or more modified nucleotides.

In some embodiments, the relative amounts of the lipid component and the modified RNA in a nanoparticle may vary. In some embodiments, the wt/wt ratio of the lipid component to the modified RNA in a nanoparticle may be from about 5:1 to about 100:1, such as 5:1, 6:1, 7:1, 8:1, 9:1, 10:1, 11:1, 12:1, 13:1, 14:1, 15:1, 16:1, 17:1, 18:1, 19:1, 20:1, 25:1, 30:1, 35:1, 40:1, 45:1, 50:1, 60:1, 70:1, 80:1, 90:1, and 100:1. For example, the wt/wt ratio of the lipid component to the modified RNA may be from about 10:1 to about 40:1. In some embodiments, the wt/wt ratio is about 20:1. In some embodiments, the wt/wt ratio is about 10:1.

In some embodiments, the relative amounts of the lipid component and the modified RNA in a nanoparticle may be provided by a specific N:P ratio. The N:P ratio of the composition refers to the molar ratio of nitrogen atoms in one or more lipids to the number of phosphate groups in an RNA. In general, a lower N:P ratio is preferred. In some embodiments, the N:P ratio may be from about 2:1 to about 30:1, such as 2:1, 3:1, 4:1, 5:1, 6:1, 7:1, 8:1, 9:1, 10:1, 12:1, 14:1, 16:1, 18:1, 20:1, 22:1, 24:1, 26:1, 28:1, or 30:1. In some embodiments, the N:P ratio may be from about 2:1 to about 8:1. For example, the N:P ratio may be about 3.0:1, about 3.5:1, about 4.0:1, about 4.5:1, about 5.0:1, about 5.5:1, about 5.67:1, about 6.0:1, about 6.5:1, or about 7.0:1.

In some embodiments, the N:P ratio may be about 3:1. In some embodiments, the N:P ratio may be about 5.67:1.

Lipid nanoparticles can be prepared using methods well-known in the art (see, e.g., Belliveau et al., "Microfluidic synthesis of highly potent limit-size lipid nanoparticles for in vivo delivery of siRNA," Mol. Ther. Nucleic Acids, 2012, 1(8):e37; Zhigaltsev et al., Bottom-up design and synthesis of limit size lipid nanoparticle systems with aqueous and triglyceride cores using millisecond microfluidic mixing," Langmuir, 2012, 28(7):3633-3640).

In some embodiments, nanoparticles may additionally comprise a pharmaceutically acceptable excipient, which, as used herein, includes, but is not limited to, any and all solvents, dispersion media, diluents, or other liquid vehicles, dispersion or suspension aids, surface active agents, isotonic agents, thickening or emulsifying agents, preservatives, and the like, as suited to the particular dosage form desired. Excipients can also include, without limitation, polymers, core-shell nanoparticles, peptides, proteins, cells, hyaluronidase, nanoparticle mimics and combinations thereof. Various excipients for formulating pharmaceutical compositions and techniques for preparing the composition are known in the art (see Remington: The Science and Practice of Pharmacy, $22^{nd}$ Edition, Edited by Allen, Loyd V., Jr, Pharmaceutical Press; incorporated herein by reference in its entirety). The use of a conventional excipient medium may be contemplated within the scope of the present disclosure, except insofar as any conventional excipient medium may be incompatible with a substance or its derivatives, such as by producing any undesirable biological effect or otherwise interacting in a deleterious manner with any other component(s) of the pharmaceutical composition.

In some embodiments, nanoparticles may comprise a pharmaceutically effective amount of a lipid component and a modified RNA, wherein the compositions further comprise a pharmaceutically acceptable excipient. In some embodiments, the pharmaceutically acceptable excipient is chosen from a solvent, dispersion media, diluent, dispersion, suspension aid, surface active agent, isotonic agent, thickening or emulsifying agent, preservative, core-shell nanoparticles, polymer, peptide, protein, cell, hyaluronidase, and mixtures thereof. In some embodiments, the solvent is an aqueous solvent. In some embodiments, the solvent is a non-aqueous solvent.

The present disclosure also provides for a pharmaceutical composition comprises one or more lipid nanoparticles comprising a lipid component and a modified RNA as disclosed herein, and a pharmaceutically acceptable excipient. In some embodiments, pharmaceutical compositions comprise a plurality of lipid nanoparticles as disclosed herein and a pharmaceutically acceptable excipient. In some embodiments, the pharmaceutically acceptable excipient is chosen from a solvent, dispersion media, diluent, dispersion, suspension aid, surface active agent, isotonic agent, thickening or emulsifying agent, preservative, core-shell nanoparticles, polymer, peptide, protein, cell, hyaluronidase, and mixtures thereof. In some embodiments, the solvent is an aqueous solvent. In some embodiments, the solvent is a non-aqueous solvent.

7.5. Improving Wound Healing in a Subject

VEGF-A pathways play a central role in wound healing processes, including revascularization of damaged tissues, improving vascular permeability, and formation of new blood vessels. It is an aim of the present disclosure to treat subjects who suffers from diseases resulting from defective wound healing processes.

In some embodiments, nanoparticles according to this disclosure are administered to a subject who suffers from a disease that affects vascular structures. Vascular structures are most commonly injured by penetrating trauma, burns, or surgery. Diabetes impairs numerous components of wound healing, and a patient with diabetic wound healing generally has altered blood flow due to vascular dysfunction. Accordingly, a subject with skin ulcer including diabetic ulcers usually has decreased or delayed wound healing. In some embodiments, nanoparticles as disclosed herein are administered to a subject who suffers from diabetes. In the context of this disclosure, a wound can be, for example, a surgical wound, a burn, an abrasive wound, a skin biopsy site, a chronic wound, an injury (e.g., a traumatic injury wound), a graft wound, a diabetic wound, a diabetic ulcer (e.g., diabetic foot ulcer), a pressure ulcer, bed sore, and combinations thereof.

In some embodiments, nanoparticles comprising a lipid component and a modified RNA (e.g., SEQ ID NO: 1, SEQ ID NO: 3, SEQ ID NO: 4, or SEQ ID NO: 5) may be used to improve wound healing in a mammalian tissue or a subject.

In some embodiments, nanoparticles as disclosed herein may be used to induce neovascularization in a mammalian tissue or a subject. In some embodiments, nanoparticles as disclosed herein may be used to induce angiogenesis in a mammalian tissue or a subject.

Yet in some embodiments, nanoparticles as disclosed herein may be used to treat a vascular injury from trauma or surgery. In some embodiments, nanoparticles as disclosed herein may be used to treat a disease involving skin grafting and tissue grafting.

Other aspects of the disclosure relate to administration of the nanoparticles to subjects in need thereof. In some embodiments, nanoparticles as disclosed herein are administered via an intradermal route to improve wound healing of a mammalian tissue or a subject.

In certain embodiments, nanoparticles as disclosed herein may be administered at dosage levels sufficient to deliver from about 0.0001 mg/kg to about 100 mg/kg, from about 0.001 mg/kg to about 0.05 mg/kg, from about 0.005 mg/kg to about 0.05 mg/kg, from about 0.001 mg/kg to about 0.005 mg/kg, from about 0.05 mg/kg to about 0.5 mg/kg, from about 0.01 mg/kg to about 50 mg/kg, from about 0.1 mg/kg to about 40 mg/kg, from about 0.5 mg/kg to about 30 mg/kg, from about 0.01 mg/kg to about 10 mg/kg, from about 0.1 mg/kg to about 10 mg/kg, or from about 1 mg/kg to about 25 mg/kg, of modified RNA per subject body weight per day, one or more times a day, to obtain the desired therapeutic effect.

In some embodiments, nanoparticles as disclosed herein are administered to a subject in a single administration. In some embodiments, nanoparticles as disclosed herein are administered to the subject, at a fixed-dosage in multiple (e.g., two, three, four, five, six, seven, eight, nine, ten, eleven, twelve, thirteen, fourteen, fifteen, sixteen, seventeen, eighteen, nineteen, twenty, or more) administrations. In each of the embodiments in this paragraph, the "multiple administrations" can be separated from each other by short (1-5 mins), medium (6-30 minutes), or long (more than 30 minutes, hours, or even days) intervals of time.

The nanoparticles may be administered to a subject using any dosage of administration effective for treating a disease, disorder, and/or condition. The exact dosage required will vary from subject to subject, depending on the species, age, and general condition of the subject, the severity of the disease, the particular formulation, its mode of administration, its mode of activity, and the like. It will be understood, however, that the total daily usage of the compositions may be decided by the attending physician within the scope of sound medical judgment. The specific pharmaceutically effective dose level for any particular patient will depend upon a variety of factors including the severity of the disease, the specific composition employed, the age, body weight, general health, sex and diet of the patient, the time of administration, route of administration, the duration of the treatment, and like factors well-known in the medical arts.

All of the claims in the claim listing are herein incorporated by reference into the specification in their entireties as additional embodiments.

8. EXAMPLES

8.1. Example 1

Preparation of Nanoparticle and Citrate Saline Compositions

Lipids and modified RNAs: Stock solution of lipids in ethanol were prepared from Compound A, distearoyl phosphatidylcholine (DSPC, Avanti Polar Lipids), cholesterol (Sigma), and a polyethylene glycol modified lipid (mPEG$_{2000}$-DMG from NOF Corporation). The lipids were mixed in ethanol 99.5% to a total lipid concentration of 12.5 mM. The composition was Compound A, DSPC, Cholesterol, DMG-PEG at the ratio of 50:10:38.5:1.5% mol. The VEGF-A modified RNA (e.g., SEQ ID NO: 1, SEQ ID NO: 3, SEQ ID NO: 4, or SEQ ID NO: 5) was thawed and diluted to 6.25 mM in sodium acetate buffer and HyClone water at concentrations corresponding to a charge ratio (N:P) of 5.67 or 3 in the final formulation. The final formulations after dilution were as follows:

| LNP 1:11 (N:P = 3), mRNA concentration 0.06 mg/mL | |
|---|---|
| LNP Component | Amount (mg/mL) |
| VEGF-A modified RNA | 0.06 |
| Compound A | 0.37 |
| DSPC | 0.08 |
| Cholesterol | 0.16 |
| DMG-PEG | 0.04 |

| LNP 1:20 (N:P = 5.67), mRNA concentration 0.06 mg/mL | |
|---|---|
| LNP Component | Amount (mg/mL) |
| VEGF-A modified RNA | 0.06 |
| Compound A | 0.70 |
| DSPC | 0.16 |
| Cholesterol | 0.30 |
| DMG-PEG | 0.07 |

Lipid nanoparticle (LNP) compositions: The LNP compositions were prepared by rapidly mixing ethanol solution containing the lipids and aqueous solution of VEGF-A modified RNA on a microfluidic device, followed by dialysis in phosphate buffered saline (PBS). Briefly, the VEGF-A modified RNA solution and the lipid solution were injected into a microfluidic mixing device at a volumetric ratio of aqueous to ethanol 3:1 and flow rates of 12-14 mL/min using two syringes, which were controlled by syringe pumps. Ethanol was removed by dialyzing LNP compositions against PBS buffer overnight using membranes with 10 KD cutoff. LNP compositions were concentrated by using centrifugation filter devices with 30 KD cutoff and characterized by particle size (72 nm), VEGF-A modified RNA concentration (0.35 mg/mL), polydispersity index (0.14) and encapsulation (94%). LNP compositions were diluted to final concentrations of 0.33 mg/mL with PBS and filtered sterile. LNP compositions were stored refrigerated.

Citrate saline compositions: Citrate saline compositions were prepared by diluting thawed VEGF-A modified RNA solution with HyClone water and a concentrated buffer solution to a final composition of 10 mM sodium citrate and 130 mM sodium chloride at pH 6.5.

8.2. Example 2

Assessment of Human VEGF-A Protein Production Following Intradermal Injection of Human VEGF-A Modified RNA in Mouse Nanoparticle and citrate saline compositions comprising a VEGF-A modified RNA and Compound A were prepared as in Example 1. In this example, the VEGF-A modified RNA had the sequence of SEQ ID NO: 3.

Male db/db mice (C57BL/6J, BKS.Cg-m+/+Leprdb/ BomTac Homozygous, Taconic Denmark) were anesthetized with isoflurane. These mice are an established model of Type II diabetes and have impaired wound healing as compared to wild-type mice. The mice back was shaved and the remaining hair was removed with hair removal cream. Either VEGF-A modified RNA (100 μg) formulated in citrate saline or VEGF-A modified RNA (3 μg) formulated in LNP (See Example 1) was injected intradermally as 4 separate injections (10 μL each, total volume 40 μL) within an circle area of 0.785 mm$^2$. At predefined time points following the intradermal injections, the mice were anesthetized and the injected skin areas were sampled and snap frozen in liquid nitrogen and stored at 80° C. All samples were analyzed for human VEGF-A protein.

Samples from db/db mice injected with 100 μg VEGF-A modified RNA formulated in citrate saline were taken 6, 24, 48, 72, and 144 hours after injection. Samples from db/db mice injected with 3 pg VEGF-A modified RNA formulated in LNP were harvested at 3, 6, 24, 48, 72, 144 hours after injection.

Quantification of Human VEGF-A Protein in Mouse Skin

To prepare the skin samples for analysis of human VEGF-A protein content, Tris lysis buffer containing phosphatase inhibitors I and II and protease inhibitor (Meso Scale Discovery (MSD), Rockville, Md., USA) was added to the frozen tissue biopsies and frozen at approximately 20° C. prior to homogenization. Stainless steel beads (3 mm) were then added and the samples homogenized using the Precellys homogenizer instrument. The homogenates were centrifuged and the supernatants stored at 80° C. prior to analysis.

Human VEGF-A concentrations were determined using a sandwich immunoassay with electrochemical luminescent detection. MSD® 96-well MULTI-ARRAY® human VEGF-A assay kit (Mesoscale, Rockville, Md.) were used to measure the VEGF-A concentration in the tissue homogenates. This assay detects human VEGF-A protein only and thus serves to assay only VEGF-A expressed from the modified RNA. The assay was performed as per the kit instructions. Standards were serially diluted in MSD diluents. Samples with high concentration were diluted with MSD diluents prior to analysis to fit within standard curve and the plates were read on the Meso Scale Discovery's Sector Imager 6000.

Results

FIGS. 3 and 4 summarize the time profiles and magnitude of human VEGF-A protein production after intradermal injection of VEGF-A modified RNA formulated in citrate saline (100 µg) and LNP (3 µg), respectively. There was an efficient protein production within 6 and 3 hours, respectively (FIG. 4). In particular, the LNP composition resulted in the production of more than about 400 pg/mg of VEGF-A protein within 8 hours (FIG. 4). In addition, the LNP composition resulted in the production of more than about 1 pg/mg of VEGF-A protein up to 6 days (FIG. 3). Production of VEGF-A protein was substantially increased when the VEGF-A modified RNA was formulated in LNP compared to in citrate saline (FIGS. 3 and 4).

Table 2 summarizes pharmacokinetic parameters obtained after intradermal injection of VEGF-A modified RNA formulated in citrate saline (100 µg) and LNP (3 µg). The $C_{max}$ was increased 13.7-fold for VEGF-A modified RNA formulated in LNP despite the fact that the dose was only 3% of the VEGF-A modified RNA formulated in citrate saline. The total area under the concentration curve, $AUC_{0-t}$, was increased 6.6 times with 3 µg VEGF-A modified RNA formulated in LNP compared to 100 µg VEGF-A modified RNA formulated in citrate saline.

Table 2. Pharmacokinetic parameters calculated from human VEGF-A concentrations obtained in the two time series with citrate saline and LNP-formulated human VEGF-A modified RNA, respectively. The total area under the concentration curve ($AUC_{0-t}$) was calculated based on the median profile on the measured data points up to 144 hours after dose.

| Group | Dose (µg) | $T_{max}$ (h) | $C_{max}$ (pg/mg tissue) | $AUC_{(0-t)}$ (pg*h/mg tissue) | $t_{1/2}$ (h) |
|---|---|---|---|---|---|
| LNP | 3 | 6 | 424 | 5296 | 50 |
| Citrate saline | 100 | 24 | 31 | 806 | 40 |

8.3. Example 3

Effects on Wound Healing Following Intradermal Injection of Human VEGF-A Modified RNA Materials and Methods Lipid nanoparticle and citrate saline compositions comprising a VEGF-A modified RNA and Compound A were prepared as in Example 1. In this example, the VEGF-A modified RNA had the sequence of SEQ ID NO: 4. In addition, a non-translatable VEGF-A modified RNA (SEQ ID NO: 6) was used to formulate certain nanoparticle or citrate saline compositions as indicated in the figures.

Male 12 weeks old db/db mice (B6.BKS(D)-Leprdb/J) from Jackson Lab USA were analyzed for blood glucose after 4 hours fastening and then randomized into treatments groups. The mice were anaesthetized with isoflurane. The dorsal surface of each mouse was shaved with an electric clipper followed by a depilatory agent to remove any remaining hair. The skin was rinsed with descutan and ethanol. A full thickness wound on the back of each mouse was created by a mark with a 10 mm biopsy punch and then cut out under sterile conditions and covered with a Tegaderm bandage. On day 3 after wounding, the Tegaderm bandage was removed. Nanoparticle or citrate saline composition was injected intradermally as 4 separate injections (10 µL each, total volume 40 µL) at positions close to the wound edge. The wound was then covered by a new Tegaderm bandage. During the observation period the mice were kept separate to avoid interference with the wound healing.

The wound healing was determined from a time series (i.e. every 3rd/4th day up to day 17 post wounding) of digital photographs taken at a fixed distance and with indirect illumination. The wound area was determined by tracing the wound margin using the image analyzing software Image J, and then calculated as a percent area of baseline area at day 3 after wounding just before dosing.

Statistical evaluation was done with an unpaired, two-sided t-test, and p-values<0.05 were considered significant.

Results

As shown in FIG. 5, at day 7, a lipid nanoparticle composition comprising 1 µg or 3 µg VEGF-A modified RNA significantly improved wound healing when compared to a lipid nanoparticle composition comprising 3 µg non-translatable VEGF-A as well as a citrate saline composition comprising 100 µg VEGF-A modified RNA. Furthermore, at day 10, the lipid nanoparticle composition comprising 1 µg or 3 µg VEGF-A modified RNA significantly improved wound healing when compared to the lipid nanoparticle composition comprising 3 µg non-translatable VEGF-A modified RNA. At day 10, there was no significant difference between the lipid nanoparticle composition comprising 1 µg or 3 µg VEGF-A modified RNA and the citrate saline composition comprising 100 µg VEGF-A modified RNA.

In a separate experiment, shown in FIG. 6, at day 7, a lipid nanoparticle composition comprising 3 µg VEGF-A modified RNA significantly improved wound healing when compared to a lipid nanoparticle composition comprising 3 µg non-translatable VEGF-A modified RNA as well as a citrate saline composition that does not comprise any modified RNA. Furthermore, at day 10, the lipid nanoparticle composition comprising 3 µg VEGF-A modified RNA significantly improved wound healing when compared to the lipid nanoparticle composition comprising 3 µg non-translatable VEGF-A modified RNA.

FIG. 7 shows another wound healing experiment. At day 7, a lipid nanoparticle composition comprising 3 µg VEGF-A modified RNA significantly improved wound healing when compared to a lipid nanoparticle composition comprising 3 µg GFP modified RNA, a lipid nanoparticle composition that does not comprise any modified RNA, or a citrate saline composition that does not comprise any modified RNA. Furthermore, at day 10, the lipid nanoparticle composition comprising 3 µg VEGF-A modified RNA significantly improved wound healing when compared to the lipid nanoparticle composition comprising 3 µg GFP modified RNA.

As shown in FIG. 8, at day 7 or day 10, there were no significant differences in would healing following intradermal injections of the following four compositions: (1) a lipid nanoparticle composition comprising 3 µg non-translatable VEGF-A modified RNA, (2) a citrate saline composition comprising 100 µg VEGF-A modified RNA, (3) a citrate saline composition comprising 100 µg non-translatable VEGF-A modified RNA, and (4) a citrate saline composition that does not comprise any modified RNA.

9. SEQUENCES

9.1. SEQ ID NO: 1: A modified RNA encoding VEGF-A (SEQ ID NO: 1)

5'$^{7Me}$G$_{ppp}$G$_{2'OMe}$GGAAAUAAGAGAGAAAAGAAGAGUAAGAAGAAAUAUAAGA

GCCACCAUGAACUUUCUGCUGUCUUGGGUGCAUUGGAGCCUUGCCUUGCUG

CUCUACCUCCACCAUGCCAAGUGGUCCCAGGCUGCACCCAUGGCAGAAGGA

GGAGGGCAGAAUCAUCACGAAGUGGUGAAGUUCAUGGAUGUCUAUCAGCGC

AGCUACUGCCAUCCAAUCGAGACCCUGGUGGACAUCUUCCAGGAGUACCCU

GAUGAGAUCGAGUACAUCUUCAAGCCAUCCUGUGUGCCCCUGAUGCGAUGC

GGGGGCUGCUGCAAUGACGAGGGCCUGGAGUGUGUGCCCACUGAGGAGUCC

AACAUCACCAUGCAGAUUAUGCGGAUCAAACCUCACCAAGGCCAGCACAUA

GGAGAGAUGAGCUUCCUACAGCACAACAAAUGUGAAUGCAGACCAAAGAAA

GAUAGAGCAAGACAAGAAAAUCCCUGUGGGCCUUGCUCAGAGCGGAGAAAG

CAUUUGUUUGUACAAGAUCCGCAGACGUGUAAAUGUUCCUGCAAAAACACA

GACUCGCGUUGCAAGGCGAGGCAGCUUGAGUUAAACGAACGUACUUGCAGA

UGUGACAAGCCGAGGCGGUGAUAAUAGGCUGGAGCCUCGGUGGCCAUGCUU

CUUGCCCCUUGGGCCUCCCCCCAGCCCCUCCUCCCCUUCCUGCACCCGUAC

CCCCGUGGUCUUUGAAUAAAGUCUGAGUGGGCGGCAAAAAAAAAAAAAAAA

AAAAAAAAAAAAAAAAAAAAAAAAAAAAAAAAAAAAAAAAAAAAAAAAA

AAAAAAAAAAAAAAAAAAAAAAAAAAAAAAAAAAUCUAG$_{OH}$3'

Wherein:
A, C, G & U = AMP, CMP, GMP & N1-methyl-pseudoUMP, respectively
Me = methyl
p = inorganic phosphate

9.2. SEQ ID NO: 2: Amino acid sequence of human VEGF-A isoform VEGF-165

(SEQ ID NO: 2)

MNFLLSWVHWSLALLLYLHHAKWSQAAPMAEGGGQNHHEVVKFMDVYQRS

YCHPIETLVDIFQEYPDEIEYIFKPSCVPLMRCGGCCNDEGLECVPTEES

NITMQIMRIKPHQGQHIGEMSFLQHNKCECRPKKDRARQENPCGPCSERRK

HLFVQDPQTCKCSCKNTDSRCKARQLELNERTCRCDKPRR

9.3. SEQ ID NO: 3: A modified RNA encoding VEGF-A (SEQ ID NO: 3)

5'$^{7Me}$G$_{ppp}$G$_{2'OMe}$AGGAAAUAAGAGAGAAAAGAAGAGUAAGAAGAAAUAUAAG

AGCCACCAUGAACUUUCUGCUGUCUUGGGUGCAUUGGAGCCUUGCCUUGCU

GCUCUACCUCCACCAUGCCAAGUGGUCCCAGGCUGCACCCAUGGCAGAAGG

AGGAGGGCAGAAUCAUCACGAAGUGGUGAAGUUCAUGGAUGUCUAUCAGCG

CAGCUACUGCCAUCCAAUCGAGACCCUGGUGGACAUCUUCCAGGAGUACCC

UGAUGAGAUCGAGUACAUCUUCAAGCCAUCCUGUGUGCCCCUGAUGCGAUG

CGGGGGCUGCUGCAAUGACGAGGGCCUGGAGUGUGUGCCCACUGAGGAGUC

CAACAUCACCAUGCAGAUUAUGCGGAUCAAACCUCACCAAGGCCAGCACAU

AGGAGAGAUGAGCUUCCUACAGCACAACAAAUGUGAAUGCAGACCAAAGAA

AGAUAGAGCAAGACAAGAAAAUCCCUGUGGGCCUUGCUCAGAGCGGAGAAA

GCAUUUGUUUGUACAAGAUCCGCAGACGUGUAAAUGUUCCUGCAAAAACAC

AGACUCGCGUUGCAAGGCGAGGCAGCUUGAGUUAAACGAACGUACUUGCAG

AUGUGACAAGCCGAGGCGGUGAUAAUAGGCUGGAGCCUCGGUGGCCAUGCU

-continued

UCUUGCCCCUUGGGCCUCCCCCCAGCCCCUCCUCCCCUUCCUGCACCCGUA

CCCCCGUGGUCUUUGAAUAAAGUCUGAGUGGGCGGCAAAAAAAAAAAAAAA

AAAAAAAAAAAAAAAAAAAAAAAAAAAAAAAAAAAAAAAAAAAAAAAAAA

AAAAAAAAAAAAAAAAAAAAAAAAAAAAAAAAAAUCUAG$_{OH}$3'
Wherein:
A, C, G & U= AMP, CMP, GMP & N1-methyl-pseudoUMP, respectively
Me = methyl
p = inorganic phosphate 9.4. SEQ ID NO: 4: A modified RNA encoding VEGF-A (VEGF-01-012)

(SEQ ID NO: 4)

5'$^{7Me}$G$_{ppp}$GGGAAAUAAGAGAGAAAAGAAGAGUAAGAAGAAAUAUAAGAGCC

ACCAUGAACUUUCUCCUUUCUUGGGUGCAUUGGAGCCUUGCCUUGUUACUC

UACCUCCACCACGCCAAGUGGUCCCAGGCCGCACCCAUGGCAGAAGGAGGA

GGGCAGAAUCAUCACGAAGUGGUGAAGUUCAUGGACGUCUAUCAGCGCAGC

UACUGCCAUCCAAUCGAGACACUGGUGGACAUCUUCCAGGAGUACCCUGAU

GAGAUCGAGUACAUCUUCAAGCCAUCCUGUGUGCCCCUGAUGCGAUGCGGC

GGCUGCUGCAAUGACGAGGGCCUGGAGUGUGUGCCUACUGAGGAGUCCAAC

AUCACCAUGCAGAUUAUGCGGAUCAAACCUCACCAAGGCCAGCACAUAGGA

GAGAUGAGCUUCCUACAGCACAACAAAUGUGAAUGCAGACCAAAGAAAGAU

AGAGCAAGACAAGAGAAUCCCUGUGGGCCUUGCUCAGAGCGGAGAAAGCAU

UUGUUUGUACAAGAUCCGCAGACGUGUAAAUGUUCCUGCAAGAACACAGAC

UCGCGUUGCAAGGCGAGGCAGCUUGAGUUAAACGAACGUACUUGCAGAUGU

GACAAGCCGAGGCGGUGAUAAUAGGCUGGAGCCUCGGUGGCCAUGCUUCUU

GCCCCUUGGGCCUCCCCCCAGCCCCUCCUCCCCUUCCUGCACCCGUACCCC

CGUGGUCUUUGAAUAAAGUCUGAGUGGGCGGCAAAAAAAAAAAAAAAAAA

AAAAAAAAAAAAAAAAAAAAAAAAAAAAAAAAAAAAAAAAAAAAAAAAAA

AAAAAAAAAAAAAAAAAAAAAAAAAAAAAAUCUAG3'
Wherein:
A, C, G & U = AMP, CMP, GMP & N1-methyl-pseudoUMP, respectively
p = inorganic phosphate 9.5. SEQ ID NO: 5: A modified RNA encoding VEGF-A (SEQ ID NO: 5)

5'$^{7Me}$G$_{ppp}$AGGAAAUAAGAGAGAAAAGAAGAGUAAGAAGAAAUAUAAGAGCC

ACCAUGAACUUUCUGCUGUCUUGGGUGCAUUGGAGCCUUGCCUUGCUGCUC

UACCUCCACCAUGCCAAGUGGUCCCAGGCUGCACCCAUGGCAGAAGGAGGA

GGGCAGAAUCAUCACGAAGUGGUGAAGUUCAUGGAUGUCUAUCAGCGCAGC

UACUGCCAUCCAAUCGAGACCCUGGUGGACAUCUUCCAGGAGUACCCUGAU

GAGAUCGAGUACAUCUUCAAGCCAUCCUGUGUGCCCCUGAUGCGAUGCGGG

GGCUGCUGCAAUGACGAGGGCCUGGAGUGUGUGCCCACUGAGGAGUCCAAC

AUCACCAUGCAGAUUAUGCGGAUCAAACCUCACCAAGGCCAGCACAUAGGA

GAGAUGAGCUUCCUACAGCACAACAAAUGUGAAUGCAGACCAAAGAAAGAU

AGAGCAAGACAAGAAAAUCCCUGUGGGCCUUGCUCAGAGCGGAGAAAGCAU

UUGUUUGUACAAGAUCCGCAGACGUGUAAAUGUUCCUGCAAAAACACAGAC

UCGCGUUGCAAGGCGAGGCAGCUUGAGUUAAACGAACGUACUUGCAGAUGU

GACAAGCCGAGGCGGUGAUAAUAGGCUGGAGCCUCGGUGGCCAUGCUUCUU

```
GCCCCUUGGGCCUCCCCCCAGCCCCUCCUCCCCUUCCUGCACCCGUACCCC

CGUGGUCUUUGAAUAAAGUCUGAGUGGGCGGCAAAAAAAAAAAAAAAAAAA

AAAAAAAAAAAAAAAAAAAAAAAAAAAAAAAAAAAAAAAAAAAAAAAAAAA

AAAAAAAAAAAAAAAAAAAAAAAAAAAAAAAUCUAG3'
Wherein:
A, C, G & U= AMP, CMP, GMP & N1-methyl-pseudoUMP, respectively
p = inorganic phosphate 9.6. SEQ ID NO: 6: A non-translatable VEGF-A modified RNA
                                                (SEQ ID NO: 6)
5'⁷ᴹᵉG_ppp GGGAAAUAAGAGAGAAAAGAAGAGUAAGAAGAAAUAUAAGAGCC

ACCACGAACUUUGUGCUCUCUUGGGUGCAUUGGAGCCUUGCCUUGCUGCUC

UACCUCCACCACGCCAAGUGGUCCCAGGCCGCACCCACGGCAGAAGGAGGA

GGGCAGAAUCAUCACGAAGUGGUGAAGUUCACGGACGUCUAUCAGCGCAGC

UACUGCCAUCCAAUCGAGACCCUCGUGGACAUCUUCCAGGAGUACCCUCAC

GAGAUCGAGUACAUCUUCAAGCCAUCCUGUGUGCCCCUGACGCGACGCGGG

GGCUGCUGCAACGACGAGGGCCUCGAGUGUGUGCCCACCGAGGAGUCCAAC

ACCACCACGCAGAUUACGCGGAUCAAACCUCACCAAGGCCAGCACAUAGGA

GAGACGAGCUUCCUACAGCACAACAAACGUGAACGCAGACCAAAGAAAGAU

AGAGCAAGACAAGAAAAUCCCUGUGGGCCUUGCUCAGAGCGGAGAAAGCAU

UUGUUUGUACAAGAUCCGCAGACGUGUAAACGUUCCUGCAAAAACACAGAC

UCGCGUUGCAAGGCGAGGCAGCUUGAGUUAAACGAACGUACUUGCAGACGU

GACAAGCCGAGGCGGUGAUAAUAGGUUGGAGCCUCGGUGGCCACGCUUCUU

GCCCCUUGGGCCUCCCCCCAGCCCCUCCUCCCCUUCCUGCACCCGUACCCC

CGUGGUCUUUGAAUAAAGUCUGAGUGGGCGGCAAAAAAAAAAAAAAAAAAA

AAAAAAAAAAAAAAAAAAAAAAAAAAAAAAAAAAAAAAAAAAAAAAAAAAA

AAAAAAAAAAAAAAAAAAAAAAAAAAAA3'
Wherein:
A, C, G & U = AMP, CMP, GMP & N1-methyl-pseudoUMP, respectively
p = inorganic phosphate
```

---

What is claimed is:

1. A lipid nanoparticle comprising
a modified mRNA comprising any one of SEQ ID NOs: 1 or 3-5, encoding a VEGF-A polypeptide of SEQ ID NO: 2.

2. The lipid nanoparticle of claim 1, wherein the lipid nanoparticle has a mean diameter from about 50 nm to about 100 nm.

3. A pharmaceutical composition comprising
(a) at least one lipid nanoparticle comprising
a modified mRNA comprising any one of SEQ ID NOs: 1 or 3-5, encoding a VEGF-A polypeptide of SEQ ID NO: 2; and
(b) a pharmaceutically acceptable excipient.

4. The pharmaceutical composition of claim 3, wherein the lipid nanoparticle has a mean diameter from about 50 nm to about 100 nm.

5. The pharmaceutical composition of claim 3, wherein the pharmaceutically acceptable excipient is a solvent, dispersion media, diluent, dispersion, suspension aid, surface active agent, isotonic agent, thickening or emulsifying agent, preservative, polymer, peptide, protein, cell, hyaluronidase, or mixtures thereof.

6. A method for (i) promoting and/or improving wound healing, (ii) inducing neovascularization, (iii) inducing angiogenesis, or (iv) increasing capillary and/or arteriole density comprising administering to a human subject in need thereof an effective amount of the lipid nanoparticle of claim 1.

7. The method of claim 6, wherein the lipid nanoparticle has a mean diameter from about 70 nm to about 80 nm.

8. The method of claim 6, wherein the administration results in a maximum observed plasma and/or tissue concentration ($C_{max}$) of the VEGF-A polypeptide of SEQ ID NO: 2 up to about 450 pg/ml plasma or pg/mg tissue.

9. The method of claim 6, wherein the administration results in a plasma and/or tissue total area under the concentration curve ($AUC_{0-t}$) of the VEGF-A polypeptide of SEQ ID NO: 2 up to about 5,500 pg*h/ml plasma or pg*h/mg tissue.

10. The method of claim 6, wherein the administration results in the production of more than about 400 pg/mg tissue of the VEGF-A polypeptide of SEQ ID NO: 2 within 8 hours.

11. The method of claim 6, wherein the administration results in the production of more than about 1 pg/mg tissue of the VEGF-A polypeptide of SEQ ID NO: 2 for up to 6 days.

12. The method of claim 6, wherein the lipid nanoparticle is administered intradermally.

13. The method of claim 6, wherein the concentration of the modified mRNA is from about 0.01 mg/kg to about 10 mg/kg.

14. The method of claim 6, wherein the administration results in an increase of the production of the VEGF-A polypeptide of SEQ ID NO: 2 by a factor of about 5 to about 100, when compared to an administration of the modified mRNA in a citrate saline buffer.

15. The method of claim 6, wherein the human subject suffers from diabetes.

16. The method of claim 6, wherein the human subject in need thereof has a wound, and wherein the wound is a surgical wound, a burn, an abrasive wound, a skin biopsy site, a chronic wound, an injury, a graft wound, a diabetic wound, a diabetic ulcer, a pressure ulcer, bed sore, and combinations thereof.

* * * * *

SEQUENCE LISTING

```
<160> NUMBER OF SEQ ID NOS: 6

<210> SEQ ID NO 1
<211> LENGTH: 845
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: modified_base
<222> LOCATION: (1)..(1)
<223> OTHER INFORMATION: 5' 7MeGppp, wherein Me = methyl and p =
      inorganic phosphate
<220> FEATURE:
<221> NAME/KEY: source
<223> OTHER INFORMATION: /note="Within this sequence: A = AMP, C = CMP,
      G = GMP, U = N1-methyl-pseudoUMP"
<220> FEATURE:
<221> NAME/KEY: modified_base
<222> LOCATION: (1)..(845)
<223> OTHER INFORMATION: Monophosphate or N1-methyl-pseudo monophosphate
      nucleotide
<220> FEATURE:
```

<221> NAME/KEY: modified_base
<222> LOCATION: (2)..(2)
<223> OTHER INFORMATION: G2'OMe, wherein Me is methyl
<220> FEATURE:
<221> NAME/KEY: modified_base
<222> LOCATION: (845)..(845)
<223> OTHER INFORMATION: GOH 3'
<220> FEATURE:
<221> NAME/KEY: source
<223> OTHER INFORMATION: /note="See specification as filed for detailed description of substitutions and preferred embodiments"

<400> SEQUENCE: 1

```
ggggaaauaa gagagaaaag aagaguaaga agaaauauaa gagccaccau gaacuuucug    60
cugucuuggg ugcauuggag ccuugccuug cugcucuacc uccaccaugc caaguggucc   120
caggcugcac ccauggcaga aggaggaggg cagaaucauc acgaaguggu gaaguucaug   180
gaugucuauc agcgcagcua cugccaucca aucgagaccc ugguggacau cuuccaggag   240
uacccugaug agaucgagua caucuucaag ccauccugug ucccccgau gcgaugcggg    300
ggcugcugca augacgaggg ccuggagugu gucccacug aggaguccaa caucaccaug    360
cagauuaugc ggaucaaacc ucaccaaggc cagcacauag gagagaugag cuuccuacag   420
cacaacaaau gugaaugcag accaaagaaa gauagagcaa gacaagaaaa ucccugvggg   480
ccuugcucag agcggagaaa gcauuguuu guacaagauc cgcagacgug uaaauguucc   540
ugcaaaaaca cagacucgcg uugcaaggcg aggcagcuug aguuaaacga acguacuugc   600
agaugugaca agccgaggcg ugauaauag gcuggagccu cgguggccau gcuucuugcc   660
ccuugggccu cccccagcc cuccucccc uuccugcacc cguaccccg uggucuuuga    720
auaaagucug aguggcggc aaaaaaaaa aaaaaaaaa aaaaaaaaa aaaaaaaaa        780
aaaaaaaaa aaaaaaaaa aaaaaaaaa aaaaaaaaa aaaaaaaaa aaaaaaaaa         840
ucuag                                                                845
```

<210> SEQ ID NO 2
<211> LENGTH: 191
<212> TYPE: PRT
<213> ORGANISM: Homo sapiens

<400> SEQUENCE: 2

```
Met Asn Phe Leu Leu Ser Trp Val His Trp Ser Leu Ala Leu Leu Leu
1               5                   10                  15

Tyr Leu His His Ala Lys Trp Ser Gln Ala Ala Pro Met Ala Glu Gly
                20                  25                  30

Gly Gly Gln Asn His His Glu Val Val Lys Phe Met Asp Val Tyr Gln
            35                  40                  45

Arg Ser Tyr Cys His Pro Ile Glu Thr Leu Val Asp Ile Phe Gln Glu
        50                  55                  60

Tyr Pro Asp Glu Ile Glu Tyr Ile Phe Lys Pro Ser Cys Val Pro Leu
65                  70                  75                  80

Met Arg Cys Gly Gly Cys Cys Asn Asp Glu Gly Leu Glu Cys Val Pro
                85                  90                  95

Thr Glu Glu Ser Asn Ile Thr Met Gln Ile Met Arg Ile Lys Pro His
                100                 105                 110

Gln Gly Gln His Ile Gly Glu Met Ser Phe Leu Gln His Asn Lys Cys
            115                 120                 125

Glu Cys Arg Pro Lys Lys Asp Arg Ala Arg Gln Glu Asn Pro Cys Gly
        130                 135                 140
```

Pro Cys Ser Glu Arg Arg Lys His Leu Phe Val Gln Asp Pro Gln Thr
145                 150                 155                 160

Cys Lys Cys Ser Cys Lys Asn Thr Asp Ser Arg Cys Lys Ala Arg Gln
                165                 170                 175

Leu Glu Leu Asn Glu Arg Thr Cys Arg Cys Asp Lys Pro Arg Arg
            180                 185                 190

```
<210> SEQ ID NO 3
<211> LENGTH: 846
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: modified_base
<222> LOCATION: (1)..(1)
<223> OTHER INFORMATION: 5' 7MeGppp, wherein Me = methyl and p =
      inorganic phosphate
<220> FEATURE:
<221> NAME/KEY: source
<223> OTHER INFORMATION: /note="Within this sequence: A = AMP, C = CMP,
      G = GMP, U = N1-methyl-pseudoUMP"
<220> FEATURE:
<221> NAME/KEY: modified_base
<222> LOCATION: (1)..(846)
<223> OTHER INFORMATION: Monophosphate or N1-methyl-pseudo monophosphate
      nucleotide
<220> FEATURE:
<221> NAME/KEY: modified_base
<222> LOCATION: (2)..(2)
<223> OTHER INFORMATION: G2'OMe, wherein Me is methyl
<220> FEATURE:
<221> NAME/KEY: modified_base
<222> LOCATION: (846)..(846)
<223> OTHER INFORMATION: GOH 3'
<220> FEATURE:
<221> NAME/KEY: source
<223> OTHER INFORMATION: /note="See specification as filed for detailed
      description of substitutions and preferred embodiments"

<400> SEQUENCE: 3
ggaggaaaua agagagaaaa gaagaguaag aagaaauaua agagccacca ugaacuuucu      60
gcugucuugg gugcauugga gccuugccuu gcugcucuac cuccaccaug ccaagugguc     120
ccaggcugca cccauggcag aaggaggagg gcagaaucau cacgaagugg ugaaguucau     180
ggaugucuau cagcgcagcu acugccaucc aaucgagacc cugguggaca ucuuccagga     240
guacccugau gagaucgagu acaucuucaa gccauccugu gugccccuga ugcgaugcgg     300
gggcugcugc aaugacgagg gccuggagug ugugcccacu gaggaguccca acaucaccau     360 gcagauuaug cggaucaaac cucaccaagg ccagcacaua ggagagauga gcuuccuaca     420
gcacaacaaa ugugaaugca gaccaaagaa agauagagca agacaagaaa aucccugugg     480
gccuugcuca gagcggagaa agcauuuguu uguacaagau ccgcagacgu guaaauguuc     540
cugcaaaaac acagacucgc guugcaaggc gaggcagcuu gaguuaaacg aacguacuug     600
cagaugugac aagccgaggc ggugauaaua ggcuggagcc ucgguggcca ugcuucuugc     660 cccuuggggcc uccccccagc cccuccuccc cuuccugcac ccguacccc guggucuuug     720 aauaaagucu gaguggggcgg caaaaaaaaa aaaaaaaaaa aaaaaaaaaa aaaaaaaaaa     780
aaaaaaaaaa aaaaaaaaaa aaaaaaaaaa aaaaaaaaaa aaaaaaaaaa aaaaaaaaaa     840
aucuag                                                                846

<210> SEQ ID NO 4
```

```
<211> LENGTH: 845
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: modified_base
<222> LOCATION: (1)..(1)
<223> OTHER INFORMATION: 5' 7MeGppp, wherein Me = methyl and p =
      inorganic phosphate
<220> FEATURE:
<221> NAME/KEY: source
<223> OTHER INFORMATION: /note="Within this sequence: A = AMP, C = CMP,
      G = GMP, U = N1-methyl-pseudoUMP"
<220> FEATURE:
<221> NAME/KEY: modified_base
<222> LOCATION: (1)..(845)
<223> OTHER INFORMATION: Monophosphate or N1-methyl-pseudo monophosphate
      nucleotide
<220> FEATURE:
<221> NAME/KEY: source
<223> OTHER INFORMATION: /note="See specification as filed for detailed
      description of substitutions and preferred embodiments"

<400> SEQUENCE: 4
ggggaaauaa gagagaaaag aagaguaaga agaaauauaa gagccaccau gaacuuucuc      60
cuuucuuggg ugcauuggag ccuugccuug uuacucuacc uccaccacgc caagugguuc     120
caggccgcac ccauggcaga aggaggaggg cagaaucauc acgaaguggu gaaguucaug     180
gacgucuauc agcgcagcua cugccauccca aucgagacac ugguggacau cuuccaggag     240
uacccugaug agaucgagua caucuucaag ccaccucugug ugccccugau gcgaugcggc     300
ggcugcugca augacgaggg ccuggagugu gugccuacug aggaguccaa caucaccaug     360
cagauuaugc ggaucaaacc ucaccaaggc cagcacauag gagagaugag cuuccuacag     420
cacaacaaau gugaaugcag accaaagaaa gauagagcaa gacaagagaa ucccuguggg     480
ccuugcucag agcggagaaa gcauuuguuu guacaagauc cgcagacgug uaaauguucc     540
ugcaagaaca cagacucgcg uugcaaggcg aggcagcuug aguuaaacga acguacuugc     600
agaugugaca agccgaggcg gugauaauag gcuggagccu cgguggccau gcuucuugcc     660
ccuugggccu cccccccagcc ccuccucccc uuccugcacc cguaccccg uggucuuuga     720 auaaagucug aguggggcggc aaaaaaaaaa aaaaaaaaaa aaaaaaaaaa aaaaaaaaaa     780
aaaaaaaaaa aaaaaaaaaa aaaaaaaaaa aaaaaaaaaa aaaaaaaaaa aaaaaaaaaa     840
ucuag                                                                845

<210> SEQ ID NO 5
<211> LENGTH: 845
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: modified_base
<222> LOCATION: (1)..(1)
<223> OTHER INFORMATION: 5' 7MeGppp, wherein Me = methyl and p =
      inorganic phosphate
<220> FEATURE:
<221> NAME/KEY: source
<223> OTHER INFORMATION: /note="Within this sequence: A = AMP, C = CMP,
      G = GMP, U = N1-methyl-pseudoUMP"
<220> FEATURE:
<221> NAME/KEY: modified_base
<222> LOCATION: (1)..(845)
```

```
<223> OTHER INFORMATION: Monophosphate or N1-methyl-pseudo monophosphate
      nucleotide
<220> FEATURE:
<221> NAME/KEY: source
<223> OTHER INFORMATION: /note="See specification as filed for detailed
      description of substitutions and preferred embodiments"

<400> SEQUENCE: 5
gaggaaauaa gagagaaaag aagaguaaga agaaauauaa gagccaccau gaacuuucug       60
cugucuuggg ugcauuggag ccuugccuug cugcucuacc uccaccaugc caaguggucc      120
caggcugcac ccauggcaga aggaggaggg cagaaucauc acgaaguggu gaaguucaug      180
gaugucuauc agcgcagcua cugccaucca aucgagaccc ugguggacau cuuccaggag      240
uacccugaug agaucgagua caucuucaag ccauccugug ugccccugau gcgaugcggg      300
ggcugcugca augacgaggg ccuggagugu gugcccacug aggagccaa caucaccaug       360 cagauuaugc ggaucaaacc ucaccaaggc cagcacauag gagagaugag cuuccuacag      420
cacaacaaau gugaaugcag accaaagaaa gauagagcaa gacaagaaaa ucccuguggg      480
ccuugcucag agcggagaaa gcauuuguuu guacaagauc cgcagacgug uaaauguucc      540
ugcaaaaaca cagacucgcg uugcaaggcg aggcagcuug aguuaaacga acguacuugc      600
agaugugaca agccgaggcg gugauaauag gcuggagccu cgguggccau gcuucuugcc      660
ccuugggccu cccccccagcc ccuccucccc uuccugcacc cguaccccg uggucuuuga       720 auaaagucug aguggggcggc aaaaaaaaaa aaaaaaaaaa aaaaaaaaaa aaaaaaaaaa     780
aaaaaaaaaa aaaaaaaaaa aaaaaaaaaa aaaaaaaaaa aaaaaaaaaa aaaaaaaaaa     840
ucuag                                                                 845

<210> SEQ ID NO 6
<211> LENGTH: 840
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: modified_base
<222> LOCATION: (1)..(1)
<223> OTHER INFORMATION: 5' 7MeGppp, wherein Me = methyl and p =
      inorganic phosphate
<220> FEATURE:
<221> NAME/KEY: source
<223> OTHER INFORMATION: /note="Within this sequence: A = AMP, C = CMP,
      G = GMP, U = N1-methyl-pseudoUMP"
<220> FEATURE:
<221> NAME/KEY: modified_base
<222> LOCATION: (1)..(840)
<223> OTHER INFORMATION: Monophosphate or N1-methyl-pseudo monophosphate
      nucleotide
<220> FEATURE:
<221> NAME/KEY: source
<223> OTHER INFORMATION: /note="See specification as filed for detailed
      description of substitutions and preferred embodiments"

<400> SEQUENCE: 6
ggggaaauaa gagagaaaag aagaguaaga agaaauauaa gagccaccac gaacuuugug       60
cucucuuggg ugcauuggag ccuugccuug cugcucuacc uccaccacgc caaguggucc      120
caggccgcac ccacggcaga aggaggaggg cagaaucauc acgaaguggu gaaguucacg      180
gacgucuauc agcgcagcua cugccaucca aucgagaccc ucguggacau cuuccaggag      240
uacccucacg agaucgagua caucuucaag ccauccugug ugccccugac gcgacgcggg      300
```

```
ggcugcugca acgacgaggg ccucgagugu gugcccaccg aggaguccaa caccaccacg    360
cagauuacgc ggaucaaacc ucaccaaggc cagcacauag gagagacgag cuuccuacag    420
cacaacaaac gugaacgcag accaaagaaa gauagagcaa gacaagaaaa ucccuguggg    480
ccuugcucag agcggagaaa gcauuuguuu guacaagauc cgcagacgug uaaacguucc    540
ugcaaaaaca cagacucgcg uugcaaggcg aggcagcuug aguuaaacga acguacuugc    600
agacgugaca agccgaggcg gugauaauag guuggagccu cgguggccac gcuucuugcc    660
ccuugggccu cccccagcc ccuccuccc uuccugcacc cguacccccg uggucuuuga     720
auaaagucug aguggcggc aaaaaaaaa aaaaaaaaaa aaaaaaaaaa aaaaaaaaaa     780
aaaaaaaaaa aaaaaaaaaa aaaaaaaaaa aaaaaaaaaa aaaaaaaaaa aaaaaaaaaa   840
```